US012746003B2

(12) United States Patent
Wellman

(10) Patent No.: US 12,746,003 B2
(45) Date of Patent: Sep. 29, 2026

(54) SURGICAL INSTRUMENT WITH ADJUSTABLE JAWS

(71) Applicant: Intuitive Surgical Operations, Inc., Sunnyvale, CA (US)

(72) Inventor: Ashley Wellman, East Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/923,210

(22) Filed: Oct. 22, 2024

(65) Prior Publication Data

US 2025/0040930 A1 Feb. 6, 2025

Related U.S. Application Data

(63) Continuation of application No. 17/764,918, filed as application No. PCT/US2020/054568 on Oct. 7, 2020, now Pat. No. 12,156,654.

(Continued)

(51) Int. Cl.
*A61B 17/072* (2006.01)
*A61B 34/30* (2016.01)

(52) U.S. Cl.
CPC ........ *A61B 17/07207* (2013.01); *A61B 34/30* (2016.02); *A61B 2017/0725* (2013.01);

(Continued)

(58) Field of Classification Search
CPC .. A61B 2017/0725; A61B 2017/07271; A61B 2017/07278; A61B 2017/07285;

(Continued)

(56) References Cited

U.S. PATENT DOCUMENTS

| | | | |
|---|---|---|---|
| 75,364 | A | 3/1868 | Case |
| 3,792,597 | A | 2/1974 | Orain et al. |

(Continued)

FOREIGN PATENT DOCUMENTS

| | | | |
|---|---|---|---|
| AU | 2014259544 | A1 | 9/2015 |
| CN | 103889344 | A | 6/2014 |

(Continued)

OTHER PUBLICATIONS

Burstein M.D., “8 MM Sureform 30 Staplers and Reloads,” Sages, Jun. 2022, 1 Page. Retrieved from internet URL: https://www.accessdata.fda.gov/cdrh_docs/pdf21/K211997.pdf.

(Continued)

*Primary Examiner* — Linda J. Hodge
(74) *Attorney, Agent, or Firm* — Farber LLC

(57) ABSTRACT

A surgical instrument, such as a tissue sealing instrument, is provided with an end effector having first and second movable jaws that define a gap therebetween in the closed position for clamping, sealing and/or stapling tissue. The jaws are movable relative to each other in the closed position to reduce a thickness of least one portion of this gap. This configuration allows the jaws to be moved closer together to reduce the overall size of the instrument when, for example, the instrument is introduced and retracted through an opening in the patient, or maneuvered within a body cavity. The surgical instrument may also have multiple settings for use with different staple cartridges, while still maintaining a fixed dimension between the two jaws for clamping, stapling and/or sealing tissue, providing a more adaptable surgical instrument that allows the surgeon to use different staple cartridges without having to change surgical instruments.

19 Claims, 18 Drawing Sheets

Related U.S. Application Data

(60) Provisional application No. 62/916,860, filed on Oct. 18, 2019, provisional application No. 62/916,864, filed on Oct. 18, 2019.

(52) U.S. Cl.
CPC ............... *A61B 2017/07271* (2013.01); *A61B 2017/07278* (2013.01); *A61B 2017/07285* (2013.01)

(58) Field of Classification Search
CPC .......... A61B 34/30; A61B 2017/07242; A61B 2017/07257; A61B 2017/07264; A61B 17/285; A61B 17/295
See application file for complete search history.

(56) References Cited

U.S. PATENT DOCUMENTS

| | | | |
|---|---|---|---|
| D231,902 | S | 6/1974 | Olson |
| D236,083 | S | 7/1975 | Robert |
| D236,427 | S | 8/1975 | Olson |
| 4,305,539 | A | 12/1981 | Korolkov et al. |
| 4,319,576 | A | 3/1982 | Rothfuss |
| 4,352,276 | A | 10/1982 | Smith |
| 4,403,892 | A | 9/1983 | Kane |
| 4,407,286 | A | 10/1983 | Noiles et al. |
| 4,429,695 | A | 2/1984 | Green |
| 4,509,518 | A | 4/1985 | McGarry et al. |
| 4,509,932 | A | 4/1985 | Weible |
| 4,605,001 | A | 8/1986 | Rothfuss et al. |
| 4,608,981 | A | 9/1986 | Rothfuss et al. |
| 4,610,383 | A | 9/1986 | Rothfuss et al. |
| 4,633,874 | A | 1/1987 | Chow et al. |
| 4,767,044 | A | 8/1988 | Green |
| 4,809,695 | A | 3/1989 | Gwathmey et al. |
| 4,848,637 | A | 7/1989 | Pruitt |
| 4,892,244 | A | 1/1990 | Fox et al. |
| 4,930,503 | A | 6/1990 | Pruitt |
| 4,978,049 | A | 12/1990 | Green |
| 5,007,300 | A | 4/1991 | Siva |
| 5,027,834 | A | 7/1991 | Pruitt |
| 5,040,715 | A | 8/1991 | Green et al. |
| 5,133,735 | A | 7/1992 | Slater et al. |
| 5,133,736 | A | 7/1992 | Bales, Jr. et al. |
| 5,142,931 | A | 9/1992 | Menahem |
| 5,147,357 | A | 9/1992 | Rose et al. |
| 5,180,092 | A | 1/1993 | Crainich |
| 5,242,457 | A | 9/1993 | Akopov et al. |
| 5,275,323 | A | 1/1994 | Schulze et al. |
| 5,307,976 | A | 5/1994 | Olson et al. |
| 5,312,023 | A | 5/1994 | Green et al. |
| 5,316,435 | A | 5/1994 | Mozingo |
| 5,334,183 | A | 8/1994 | Wuchinich |
| 5,342,395 | A | 8/1994 | Jarrett et al. |
| 5,342,396 | A | 8/1994 | Cook |
| 5,366,133 | A | 11/1994 | Geiste |
| 5,452,836 | A | 9/1995 | Huitema et al. |
| 5,452,837 | A | 9/1995 | Williamson, IV et al. |
| 5,465,895 | A | 11/1995 | Knodel et al. |
| 5,480,089 | A | 1/1996 | Blewett |
| 5,484,095 | A | 1/1996 | Green et al. |
| 5,484,451 | A | 1/1996 | Akopov et al. |
| 5,487,500 | A | 1/1996 | Knodel et al. |
| 5,497,931 | A | 3/1996 | Nakamura |
| 5,533,521 | A | 7/1996 | Granger |
| 5,540,375 | A | 7/1996 | Bolanos et al. |
| 5,554,164 | A | 9/1996 | Wilson et al. |
| 5,560,530 | A | 10/1996 | Bolanos et al. |
| 5,562,239 | A | 10/1996 | Boiarski et al. |
| 5,564,615 | A | 10/1996 | Bishop et al. |
| 5,571,116 | A | 11/1996 | Bolanos et al. |
| 5,571,285 | A | 11/1996 | Chow et al. |
| 5,573,534 | A | 11/1996 | Stone |
| 5,573,543 | A | 11/1996 | Akopov et al. |
| 5,607,449 | A | 3/1997 | Tontarra |
| 5,615,820 | A | 4/1997 | Viola |
| 5,624,452 | A | 4/1997 | Yates |
| 5,628,446 | A | 5/1997 | Geiste et al. |
| 5,632,432 | A | 5/1997 | Schulze et al. |
| 5,651,491 | A | 7/1997 | Heaton et al. |
| 5,652,849 | A | 7/1997 | Conway et al. |
| 5,667,626 | A | 9/1997 | Cayford et al. |
| 5,673,840 | A | 10/1997 | Schulze et al. |
| 5,673,842 | A | 10/1997 | Bittner et al. |
| 5,676,674 | A | 10/1997 | Bolanos et al. |
| 5,688,269 | A | 11/1997 | Newton et al. |
| 5,690,269 | A | 11/1997 | Bolanos et al. |
| 5,693,042 | A | 12/1997 | Boiarski et al. |
| 5,697,542 | A | 12/1997 | Knodel et al. |
| 5,700,270 | A | 12/1997 | Peyser et al. |
| 5,700,276 | A | 12/1997 | Benecke |
| 5,704,534 | A | 1/1998 | Huitema et al. |
| 5,709,680 | A | 1/1998 | Yates et al. |
| 5,738,474 | A | 4/1998 | Blewett |
| 5,752,644 | A | 5/1998 | Bolanos et al. |
| 5,752,973 | A | 5/1998 | Kieturakis et al. |
| 5,762,255 | A | 6/1998 | Chrisman et al. |
| 5,762,256 | A | 6/1998 | Mastri et al. |
| 5,779,130 | A | 7/1998 | Alesi et al. |
| 5,782,396 | A | 7/1998 | Mastri et al. |
| 5,792,135 | A | 8/1998 | Madhani et al. |
| 5,820,009 | A | 10/1998 | Melling et al. |
| 5,826,776 | A | 10/1998 | Schulze et al. |
| 5,833,695 | A | 11/1998 | Yoon |
| 5,865,361 | A | 2/1999 | Milliman et al. |
| 5,871,135 | A | 2/1999 | Williamson, IV et al. |
| 5,911,353 | A | 6/1999 | Bolanos et al. |
| 5,915,616 | A | 6/1999 | Viola et al. |
| 5,919,198 | A | 7/1999 | Graves, Jr. et al. |
| 5,941,442 | A | 8/1999 | Geiste et al. |
| 5,954,259 | A | 9/1999 | Viola et al. |
| 5,959,892 | A | 9/1999 | Lin et al. |
| 6,032,849 | A | 3/2000 | Mastri et al. |
| 6,050,996 | A | 4/2000 | Schmaltz et al. |
| 6,079,606 | A | 6/2000 | Milliman et al. |
| 6,113,598 | A | 9/2000 | Baker |
| 6,126,666 | A | 10/2000 | Trapp et al. |
| 6,174,309 | B1 | 1/2001 | Wrublewski et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,312,426 | B1 | 11/2001 | Goldberg et al. |
| 6,330,956 | B1 | 12/2001 | Willinger |
| 6,330,965 | B1 | 12/2001 | Milliman et al. |
| 6,443,973 | B1 | 9/2002 | Whitman |
| 6,488,196 | B1 | 12/2002 | Fenton, Jr. |
| 6,503,259 | B2 | 1/2003 | Huxel et al. |
| 6,582,451 | B1 | 6/2003 | Marucci et al. |
| 6,585,735 | B1 | 7/2003 | Frazier et al. |
| 6,644,532 | B2 | 11/2003 | Green et al. |
| 6,656,193 | B2 | 12/2003 | Grant et al. |
| 6,669,073 | B2 | 12/2003 | Milliman et al. |
| 6,692,363 | B1 | 2/2004 | Heutschi et al. |
| 6,770,072 | B1 | 8/2004 | Truckai et al. |
| 6,783,524 | B2 | 8/2004 | Anderson et al. |
| 6,786,382 | B1 | 9/2004 | Hoffman |
| 6,793,652 | B1 | 9/2004 | Whitman et al. |
| 6,817,974 | B2 | 11/2004 | Cooper et al. |
| 6,840,938 | B1 | 1/2005 | Morley et al. |
| 6,877,647 | B2 | 4/2005 | Green et al. |
| 6,905,057 | B2 | 6/2005 | Swayze et al. |
| 6,953,139 | B2 | 10/2005 | Milliman et al. |
| 6,955,608 | B1 | 10/2005 | Lutz |
| 6,959,852 | B2 | 11/2005 | Shelton, IV et al. |
| 6,964,363 | B2 | 11/2005 | Wales et al. |
| 6,978,921 | B2 | 12/2005 | Shelton, IV et al. |
| 6,978,922 | B2 | 12/2005 | Bilotti et al. |
| 6,981,941 | B2 | 1/2006 | Whitman et al. |
| 6,985,133 | B1 | 1/2006 | Rodomista et al. |
| 6,986,451 | B1 | 1/2006 | Mastri et al. |
| 6,988,649 | B2 | 1/2006 | Shelton, IV et al. |
| 7,000,818 | B2 | 2/2006 | Shelton, IV et al. |
| 7,000,819 | B2 | 2/2006 | Swayze et al. |

(56) References Cited

U.S. PATENT DOCUMENTS

| | | | |
|---|---|---|---|
| 7,044,352 | B2 | 5/2006 | Shelton, IV et al. |
| 7,044,353 | B2 | 5/2006 | Mastri et al. |
| 7,055,730 | B2 | 6/2006 | Ehrenfels et al. |
| 7,055,731 | B2 | 6/2006 | Shelton, IV et al. |
| 7,059,508 | B2 | 6/2006 | Shelton, IV et al. |
| 7,070,083 | B2 | 7/2006 | Jankowski |
| 7,114,642 | B2 | 10/2006 | Whitman |
| 7,128,253 | B2 | 10/2006 | Mastri et al. |
| 7,140,527 | B2 | 11/2006 | Ehrenfels et al. |
| 7,140,528 | B2 | 11/2006 | Shelton, IV et al. |
| 7,258,262 | B2 | 8/2007 | Mastri et al. |
| 7,296,722 | B2 | 11/2007 | Ivanko |
| 7,308,998 | B2 | 12/2007 | Mastri et al. |
| 7,328,828 | B2 | 2/2008 | Ortiz et al. |
| 7,380,695 | B2 | 6/2008 | Doll et al. |
| 7,380,696 | B2 | 6/2008 | Shelton, IV et al. |
| 7,398,908 | B2 | 7/2008 | Holsten et al. |
| 7,401,721 | B2 | 7/2008 | Holsten et al. |
| 7,407,075 | B2 | 8/2008 | Holsten et al. |
| 7,455,676 | B2 | 11/2008 | Holsten et al. |
| 7,472,814 | B2 | 1/2009 | Mastri et al. |
| 7,481,349 | B2 | 1/2009 | Holsten et al. |
| 7,491,202 | B2 | 2/2009 | Odom et al. |
| 7,494,039 | B2 | 2/2009 | Racenet et al. |
| 7,561,141 | B2 | 7/2009 | Shahoian et al. |
| 7,565,993 | B2 | 7/2009 | Milliman et al. |
| 7,588,174 | B2 | 9/2009 | Holsten et al. |
| 7,654,431 | B2 | 2/2010 | Hueil et al. |
| 7,658,312 | B2 | 2/2010 | Vidal et al. |
| 7,673,783 | B2 | 3/2010 | Morgan et al. |
| 7,699,835 | B2 | 4/2010 | Lee et al. |
| 7,721,930 | B2 | 5/2010 | McKenna et al. |
| 7,726,539 | B2 | 6/2010 | Holsten et al. |
| 7,770,774 | B2 | 8/2010 | Mastri et al. |
| 7,780,577 | B2 | 8/2010 | Arnold |
| 7,794,475 | B2 | 9/2010 | Hess et al. |
| 7,832,611 | B2 | 11/2010 | Boyden et al. |
| 7,837,079 | B2 | 11/2010 | Holsten et al. |
| 7,866,526 | B2 | 1/2011 | Green et al. |
| 7,942,303 | B2 | 5/2011 | Shah et al. |
| 7,950,561 | B2 | 5/2011 | Aranyi |
| 8,070,035 | B2 | 12/2011 | Holsten et al. |
| 8,083,118 | B2 | 12/2011 | Milliman et al. |
| 8,127,975 | B2 | 3/2012 | Olson et al. |
| 8,157,152 | B2 | 4/2012 | Holsten et al. |
| 8,272,553 | B2 | 9/2012 | Mastri et al. |
| 8,308,042 | B2 | 11/2012 | Aranyi |
| 8,348,127 | B2 | 1/2013 | Marczyk |
| 8,365,972 | B2 | 2/2013 | Aranyi et al. |
| 8,371,492 | B2 | 2/2013 | Aranyi et al. |
| 8,439,246 | B1 | 5/2013 | Knodel |
| 8,490,851 | B2 | 7/2013 | Blier et al. |
| 8,551,091 | B2 | 10/2013 | Couture et al. |
| 8,573,465 | B2 | 11/2013 | Shelton, IV |
| 8,579,178 | B2 | 11/2013 | Holsten et al. |
| 8,608,047 | B2 | 12/2013 | Holsten et al. |
| 8,672,206 | B2 | 3/2014 | Aranyi et al. |
| 8,672,939 | B2 | 3/2014 | Garrison |
| 8,685,016 | B2 | 4/2014 | Wham et al. |
| 8,701,960 | B1 | 4/2014 | Manoux et al. |
| 8,783,541 | B2 | 7/2014 | Shelton, IV et al. |
| 8,800,841 | B2 | 8/2014 | Ellerhorst et al. |
| 8,834,518 | B2 | 9/2014 | Faller et al. |
| 8,851,355 | B2 | 10/2014 | Aranyi et al. |
| 8,852,174 | B2 | 10/2014 | Burbank |
| 8,858,547 | B2 | 10/2014 | Brogna |
| 8,864,010 | B2 | 10/2014 | Williams |
| 8,876,857 | B2 | 11/2014 | Burbank |
| 8,905,287 | B2 | 12/2014 | Racenet et al. |
| 8,925,785 | B2 | 1/2015 | Holsten et al. |
| 9,010,606 | B2 | 4/2015 | Aranyi et al. |
| 9,016,545 | B2 | 4/2015 | Aranyi et al. |
| 9,055,961 | B2 | 6/2015 | Manzo et al. |
| 9,161,807 | B2 | 10/2015 | Garrison |
| 9,192,378 | B2 | 11/2015 | Aranyi et al. |
| 9,192,379 | B2 | 11/2015 | Aranyi et al. |
| 9,211,120 | B2 | 12/2015 | Scheib et al. |
| 9,216,019 | B2 | 12/2015 | Schmid et al. |
| 9,307,986 | B2 | 4/2016 | Hall et al. |
| 9,316,267 | B2 | 4/2016 | Lenz et al. |
| 9,345,479 | B2 | 5/2016 | Racenet et al. |
| 9,498,215 | B2 | 11/2016 | Duque et al. |
| 9,681,870 | B2 | 6/2017 | Baxter, III et al. |
| 9,717,497 | B2 | 8/2017 | Zerkle et al. |
| 9,717,498 | B2 | 8/2017 | Aranyi et al. |
| 9,757,126 | B2 | 9/2017 | Cappola |
| 9,777,459 | B2 | 10/2017 | Zuritis |
| 9,808,246 | B2 | 11/2017 | Shelton, IV et al. |
| 9,877,721 | B2 | 1/2018 | Schellin et al. |
| 9,936,949 | B2 | 4/2018 | Measamer et al. |
| 10,111,659 | B2 | 10/2018 | Racenet et al. |
| 10,130,367 | B2 | 11/2018 | Cappola et al. |
| 10,231,732 | B1 | 3/2019 | Racenet et al. |
| 10,231,733 | B2 | 3/2019 | Ehrenfels et al. |
| 10,285,693 | B2 | 5/2019 | Kimsey et al. |
| D850,617 | S | 6/2019 | Shelton, IV et al. |
| 10,335,147 | B2 | 7/2019 | Rector et al. |
| 10,363,037 | B2 | 7/2019 | Aronhalt et al. |
| 10,383,628 | B2 | 8/2019 | Kang et al. |
| 10,646,219 | B2 | 5/2020 | Racenet et al. |
| 10,722,233 | B2 | 7/2020 | Wellman |
| 10,828,027 | B2 | 11/2020 | Racenet et al. |
| 10,863,988 | B2 | 12/2020 | Patel et al. |
| 10,912,556 | B2 | 2/2021 | Burbank |
| 10,973,517 | B2 | 4/2021 | Wixey |
| 11,014,224 | B2 | 5/2021 | Dey, IV et al. |
| 11,020,138 | B2 | 6/2021 | Ragosta |
| 11,166,773 | B2 | 11/2021 | Ragosta et al. |
| 11,185,331 | B2 | 11/2021 | Adams et al. |
| 11,191,542 | B2 | 12/2021 | Miller et al. |
| 11,234,700 | B2 | 2/2022 | Ragosta et al. |
| 11,266,409 | B2 | 3/2022 | Huitema et al. |
| 11,291,445 | B2 | 4/2022 | Shelton, IV et al. |
| 11,439,390 | B2 | 9/2022 | Patel et al. |
| D967,421 | S | 10/2022 | Shelton, IV et al. |
| 11,504,124 | B2 | 11/2022 | Patel et al. |
| 11,517,312 | B2 | 12/2022 | Wixey |
| 11,607,219 | B2 | 3/2023 | Shelton, IV et al. |
| 11,642,129 | B2 | 5/2023 | Burbank |
| 11,696,758 | B2 | 7/2023 | Murphy et al. |
| 11,723,661 | B2 | 8/2023 | Wixey et al. |
| 11,759,202 | B2 | 9/2023 | Morgan et al. |
| 11,786,325 | B2 | 10/2023 | Mustufa et al. |
| 11,806,015 | B2 | 11/2023 | Wixey et al. |
| 11,857,188 | B2 | 1/2024 | Hites |
| 11,864,762 | B2 | 1/2024 | Wixey |
| 11,896,224 | B2 | 2/2024 | Wellman |
| 11,903,583 | B2 | 2/2024 | Burbank et al. |
| 11,944,301 | B2 | 4/2024 | Wixey et al. |
| 11,944,302 | B2 | 4/2024 | Wixey et al. |
| 11,986,184 | B2 | 5/2024 | Patel et al. |
| 12,000,280 | B2 | 6/2024 | King |
| 12,011,168 | B2 | 6/2024 | Wixey |
| D1,035,874 | S | 7/2024 | Sun et al. |
| 12,029,426 | B2 | 7/2024 | Millman et al. |
| 12,029,473 | B2 | 7/2024 | Whitlock et al. |
| 12,089,844 | B2 | 9/2024 | Patel et al. |
| 12,137,903 | B2 | 11/2024 | Patel et al. |
| 12,156,654 | B2 | 12/2024 | Wellman |
| D1,067,431 | S | 3/2025 | Schings et al. |
| 12,251,107 | B2 | 3/2025 | Wixey et al. |
| D1,070,086 | S | 4/2025 | Yang et al. |
| 12,262,891 | B2 | 4/2025 | Burbank |
| 12,303,130 | B2 | 5/2025 | Wixey et al. |
| 12,324,589 | B2 | 6/2025 | Kerver et al. |
| 12,349,905 | B2 | 7/2025 | Wellman |
| 12,359,696 | B2 | 7/2025 | Wixey |
| 12,383,268 | B2 | 8/2025 | Wixey et al. |
| 12,402,883 | B2 | 9/2025 | Yee et al. |
| D1,097,151 | S | 10/2025 | Sun et al. |
| 2002/0165562 | A1 | 11/2002 | Grant et al. |
| 2002/0177843 | A1 | 11/2002 | Anderson et al. |
| 2002/0188293 | A1 | 12/2002 | Manzo |
| 2002/0188294 | A1 | 12/2002 | Couture et al. |

(56) References Cited

U.S. PATENT DOCUMENTS

| | | | |
|---|---|---|---|
| 2003/0078577 | A1 | 4/2003 | Truckai et al. |
| 2003/0135204 | A1 | 7/2003 | Lee et al. |
| 2003/0135205 | A1 | 7/2003 | Davenport et al. |
| 2003/0144652 | A1 | 7/2003 | Baker et al. |
| 2003/0171747 | A1 | 9/2003 | Kanehira et al. |
| 2003/0181910 | A1 | 9/2003 | Dycus et al. |
| 2004/0006340 | A1 | 1/2004 | Latterell et al. |
| 2004/0049185 | A1 | 3/2004 | Latterell et al. |
| 2004/0143263 | A1 | 7/2004 | Schechter et al. |
| 2004/0232199 | A1 | 11/2004 | Shelton et al. |
| 2004/0267310 | A1 | 12/2004 | Racenet et al. |
| 2005/0006430 | A1 | 1/2005 | Wales |
| 2005/0006434 | A1 | 1/2005 | Wales et al. |
| 2005/0021027 | A1 | 1/2005 | Shields et al. |
| 2005/0070925 | A1 | 3/2005 | Shelton, IV et al. |
| 2005/0070958 | A1 | 3/2005 | Swayze et al. |
| 2005/0101991 | A1 | 5/2005 | Ahlberg et al. |
| 2005/0113826 | A1 | 5/2005 | Johnson et al. |
| 2005/0171533 | A1 | 8/2005 | Latterell et al. |
| 2005/0178813 | A1 | 8/2005 | Swayze et al. |
| 2005/0187576 | A1 | 8/2005 | Whitman et al. |
| 2005/0273084 | A1 | 12/2005 | Hinman et al. |
| 2005/0273085 | A1 | 12/2005 | Hinman et al. |
| 2006/0000868 | A1 | 1/2006 | Shelton, IV et al. |
| 2006/0016853 | A1 | 1/2006 | Racenet |
| 2006/0020287 | A1 | 1/2006 | Lee et al. |
| 2006/0022014 | A1 | 2/2006 | Shelton, IV et al. |
| 2006/0022015 | A1 | 2/2006 | Shelton et al. |
| 2006/0024817 | A1 | 2/2006 | Deguchi et al. |
| 2006/0025809 | A1 | 2/2006 | Shelton, IV |
| 2006/0025810 | A1 | 2/2006 | Shelton, IV |
| 2006/0025811 | A1 | 2/2006 | Shelton, IV |
| 2006/0025812 | A1 | 2/2006 | Shelton, IV |
| 2006/0025813 | A1 | 2/2006 | Shelton et al. |
| 2006/0025816 | A1 | 2/2006 | Shelton, IV |
| 2006/0049230 | A1 | 3/2006 | Shelton, IV et al. |
| 2006/0097026 | A1 | 5/2006 | Shelton, IV |
| 2006/0111209 | A1 | 5/2006 | Hinman et al. |
| 2006/0111210 | A1 | 5/2006 | Hinman |
| 2006/0124689 | A1 | 6/2006 | Arad et al. |
| 2006/0161190 | A1 | 7/2006 | Gadberry et al. |
| 2006/0190031 | A1 | 8/2006 | Wales et al. |
| 2006/0199999 | A1 | 9/2006 | Ikeda et al. |
| 2006/0217706 | A1 | 9/2006 | Lau et al. |
| 2006/0217709 | A1 | 9/2006 | Couture et al. |
| 2006/0271042 | A1 | 11/2006 | Latterell et al. |
| 2007/0010838 | A1 | 1/2007 | Shelton, IV et al. |
| 2007/0045379 | A1 | 3/2007 | Shelton, IV |
| 2007/0250113 | A1 | 10/2007 | Hegeman et al. |
| 2007/0262116 | A1 | 11/2007 | Hueil et al. |
| 2007/0270884 | A1 | 11/2007 | Smith et al. |
| 2008/0023522 | A1 | 1/2008 | Olson et al. |
| 2008/0029577 | A1 | 2/2008 | Shelton et al. |
| 2008/0064572 | A1 | 3/2008 | Nardone |
| 2008/0065100 | A1 | 3/2008 | Larkin |
| 2008/0078804 | A1 | 4/2008 | Shelton et al. |
| 2008/0086114 | A1 | 4/2008 | Schmitz et al. |
| 2008/0093517 | A1 | 4/2008 | Chen |
| 2008/0108446 | A1 | 5/2008 | Faude |
| 2008/0161174 | A1 | 7/2008 | Lo |
| 2008/0196533 | A1 | 8/2008 | Bergamasco et al. |
| 2008/0210738 | A1 | 9/2008 | Shelton et al. |
| 2008/0280736 | A1 | 11/2008 | D'Eredita |
| 2008/0305934 | A1 | 12/2008 | Medina |
| 2008/0308607 | A1 | 12/2008 | Timm et al. |
| 2009/0090763 | A1 | 4/2009 | Zemlok et al. |
| 2009/0181832 | A1 | 7/2009 | Bell |
| 2009/0277947 | A1 | 11/2009 | Viola |
| 2010/0006620 | A1 | 1/2010 | Sorrentino et al. |
| 2010/0009818 | A1 | 1/2010 | Simonson et al. |
| 2010/0057081 | A1 | 3/2010 | Hanna |
| 2010/0057085 | A1 | 3/2010 | Holcomb et al. |
| 2010/0076461 | A1 | 3/2010 | Viola et al. |
| 2010/0076474 | A1 | 3/2010 | Yates et al. |
| 2010/0096431 | A1 | 4/2010 | Smith et al. |
| 2010/0108740 | A1 | 5/2010 | Pastorelli et al. |
| 2010/0145334 | A1 | 6/2010 | Olson et al. |
| 2010/0179545 | A1 | 7/2010 | Twomey et al. |
| 2010/0198248 | A1 | 8/2010 | Vakharia |
| 2010/0213240 | A1 | 8/2010 | Kostrzewski |
| 2010/0331857 | A1 | 12/2010 | Doyle et al. |
| 2011/0011915 | A1 * | 1/2011 | Shelton, IV ......... A61B 17/068 227/176.1 |
| 2011/0017801 | A1 | 1/2011 | Zemlok et al. |
| 2011/0022078 | A1 | 1/2011 | Hinman |
| 2011/0036891 | A1 | 2/2011 | Zemlok et al. |
| 2011/0042439 | A1 | 2/2011 | Johnson et al. |
| 2011/0087238 | A1 | 4/2011 | Wang et al. |
| 2011/0118707 | A1 | 5/2011 | Burbank |
| 2011/0118778 | A1 | 5/2011 | Burbank |
| 2011/0121049 | A1 | 5/2011 | Malinouskas et al. |
| 2011/0121050 | A1 | 5/2011 | Nicholas et al. |
| 2011/0139851 | A1 | 6/2011 | Mccuen |
| 2011/0152879 | A1 | 6/2011 | Williams |
| 2011/0174863 | A1 | 7/2011 | Shelton, IV et al. |
| 2011/0186614 | A1 | 8/2011 | Kasvikis |
| 2011/0204119 | A1 | 8/2011 | McCuen |
| 2011/0251613 | A1 | 10/2011 | Guerra et al. |
| 2011/0282339 | A1 | 11/2011 | Weizman et al. |
| 2011/0288573 | A1 | 11/2011 | Yates et al. |
| 2011/0290851 | A1 | 12/2011 | Shelton, IV |
| 2011/0290853 | A1 | 12/2011 | Shelton, IV et al. |
| 2011/0290854 | A1 | 12/2011 | Timm et al. |
| 2011/0290855 | A1 | 12/2011 | Moore et al. |
| 2011/0295269 | A1 | 12/2011 | Swensgard et al. |
| 2011/0295270 | A1 | 12/2011 | Giordano et al. |
| 2011/0301603 | A1 | 12/2011 | Kerr et al. |
| 2011/0319886 | A1 | 12/2011 | Chojin et al. |
| 2012/0000962 | A1 | 1/2012 | Racenet et al. |
| 2012/0022584 | A1 | 1/2012 | Donnigan et al. |
| 2012/0071891 | A1 | 3/2012 | Itkowitz et al. |
| 2012/0205419 | A1 | 8/2012 | Weir et al. |
| 2012/0209253 | A1 | 8/2012 | Donhowe |
| 2012/0223121 | A1 | 9/2012 | Viola et al. |
| 2012/0228358 | A1 | 9/2012 | Zemlok et al. |
| 2012/0248167 | A1 | 10/2012 | Flanagan et al. |
| 2012/0255986 | A1 | 10/2012 | Petty et al. |
| 2012/0265241 | A1 | 10/2012 | Hart et al. |
| 2012/0289999 | A1 | 11/2012 | Frank |
| 2012/0298719 | A1 | 11/2012 | Shelton, IV et al. |
| 2013/0015231 | A1 | 1/2013 | Kostrzewski |
| 2013/0037597 | A1 | 2/2013 | Katre et al. |
| 2013/0046303 | A1 | 2/2013 | Evans et al. |
| 2013/0056521 | A1 | 3/2013 | Swensgard |
| 2013/0068821 | A1 | 3/2013 | Huitema et al. |
| 2013/0075448 | A1 | 3/2013 | Schmid et al. |
| 2013/0087599 | A1 | 4/2013 | Krumanaker et al. |
| 2013/0098965 | A1 | 4/2013 | Kostrzewski et al. |
| 2013/0098966 | A1 | 4/2013 | Kostrzewski et al. |
| 2013/0116668 | A1 | 5/2013 | Shelton, IV et al. |
| 2013/0126586 | A1 | 5/2013 | Zhang et al. |
| 2013/0148577 | A1 | 6/2013 | Terry et al. |
| 2013/0240604 | A1 | 9/2013 | Knodel |
| 2013/0248577 | A1 | 9/2013 | Leimbach et al. |
| 2013/0256373 | A1 | 10/2013 | Schmid et al. |
| 2013/0277410 | A1 | 10/2013 | Fernandez et al. |
| 2013/0282052 | A1 | 10/2013 | Aranyi et al. |
| 2013/0296922 | A1 | 11/2013 | Allen, IV et al. |
| 2013/0327808 | A1 | 12/2013 | Chen et al. |
| 2013/0327809 | A1 | 12/2013 | Shelton, IV et al. |
| 2014/0001236 | A1 | 1/2014 | Shelton, IV et al. |
| 2014/0005653 | A1 | 1/2014 | Shelton, IV et al. |
| 2014/0005654 | A1 | 1/2014 | Batross et al. |
| 2014/0005662 | A1 | 1/2014 | Shelton, IV |
| 2014/0005677 | A1 | 1/2014 | Shelton, IV et al. |
| 2014/0021239 | A1 | 1/2014 | Kostrzewski |
| 2014/0025071 | A1 | 1/2014 | Sims et al. |
| 2014/0027492 | A1 | 1/2014 | Williams |
| 2014/0100569 | A1 | 4/2014 | Lawes et al. |
| 2014/0100600 | A1 | 4/2014 | Kendrick |
| 2014/0103093 | A1 | 4/2014 | Koch, Jr. et al. |
| 2014/0110455 | A1 | 4/2014 | Ingmanson et al. |
| 2014/0128867 | A1 | 5/2014 | Collings et al. |
| 2014/0131418 | A1 | 5/2014 | Kostrzewski |

(56) References Cited

U.S. PATENT DOCUMENTS

| | | | |
|---|---|---|---|
| 2014/0175152 | A1 | 6/2014 | Hess et al. |
| 2014/0180286 | A1 | 6/2014 | Marczyk et al. |
| 2014/0183244 | A1 | 7/2014 | Duque et al. |
| 2014/0200596 | A1 | 7/2014 | Weir et al. |
| 2014/0200612 | A1 | 7/2014 | Weir et al. |
| 2014/0200851 | A1 | 7/2014 | Weir et al. |
| 2014/0214049 | A1 | 7/2014 | Jeong et al. |
| 2014/0239036 | A1 | 8/2014 | Zerkle et al. |
| 2014/0239044 | A1 | 8/2014 | Hoffman |
| 2014/0239046 | A1 | 8/2014 | Milliman et al. |
| 2014/0246477 | A1 | 9/2014 | Koch, Jr. et al. |
| 2014/0249557 | A1 | 9/2014 | Koch, Jr. et al. |
| 2014/0257331 | A1 | 9/2014 | Kim et al. |
| 2014/0263546 | A1 | 9/2014 | Aranyi |
| 2014/0263552 | A1 | 9/2014 | Hall et al. |
| 2014/0263559 | A1 | 9/2014 | Williams et al. |
| 2014/0263565 | A1 | 9/2014 | Lytle, IV et al. |
| 2014/0263567 | A1 | 9/2014 | Williams et al. |
| 2014/0263569 | A1 | 9/2014 | Williams et al. |
| 2014/0276731 | A1 | 9/2014 | Voegele et al. |
| 2014/0276776 | A1 | 9/2014 | Parihar et al. |
| 2014/0284372 | A1 | 9/2014 | Kostrzewski |
| 2014/0305989 | A1 | 10/2014 | Parihar et al. |
| 2014/0309666 | A1 | 10/2014 | Shelton, IV et al. |
| 2014/0343550 | A1 | 11/2014 | Faller et al. |
| 2014/0343569 | A1 | 11/2014 | Turner |
| 2014/0364851 | A1 | 12/2014 | Batross et al. |
| 2015/0018856 | A1 | 1/2015 | Poo et al. |
| 2015/0073746 | A1 | 3/2015 | Gris et al. |
| 2015/0088131 | A1 | 3/2015 | Weisshaupt et al. |
| 2015/0141981 | A1 | 5/2015 | Price et al. |
| 2015/0141993 | A1 | 5/2015 | Schechter et al. |
| 2015/0173756 | A1 | 6/2015 | Baxter, III et al. |
| 2015/0173789 | A1 | 6/2015 | Baxter, III et al. |
| 2015/0209030 | A1 | 7/2015 | Kostrzewski et al. |
| 2015/0209037 | A1 | 7/2015 | Kostrzewski et al. |
| 2015/0250530 | A1 | 9/2015 | Manzo et al. |
| 2015/0256609 | A1 | 9/2015 | Morton et al. |
| 2015/0272575 | A1 | 10/2015 | Leimbach et al. |
| 2015/0272576 | A1 | 10/2015 | Cappola |
| 2015/0272583 | A1 | 10/2015 | Leimbach et al. |
| 2015/0272606 | A1 | 10/2015 | Nobis |
| 2015/0297227 | A1 | 10/2015 | Huitema et al. |
| 2015/0297230 | A1 | 10/2015 | Schellin et al. |
| 2015/0297235 | A1 | 10/2015 | Harris et al. |
| 2015/0316431 | A1 | 11/2015 | Collins et al. |
| 2015/0369277 | A1 | 12/2015 | Fevre et al. |
| 2015/0374396 | A1 | 12/2015 | Strobl et al. |
| 2016/0038227 | A1 | 2/2016 | Garrison |
| 2016/0058441 | A1 | 3/2016 | Morgan et al. |
| 2016/0058450 | A1 | 3/2016 | Shelton, IV et al. |
| 2016/0066916 | A1 | 3/2016 | Overmyer et al. |
| 2016/0089148 | A1 | 3/2016 | Harris et al. |
| 2016/0120544 | A1 | 5/2016 | Shelton, IV et al. |
| 2016/0157863 | A1 | 6/2016 | Williams et al. |
| 2016/0157926 | A1 | 6/2016 | Boudreaux |
| 2016/0166256 | A1 | 6/2016 | Baxter, III et al. |
| 2016/0174973 | A1 | 6/2016 | Shelton, IV et al. |
| 2016/0174977 | A1 | 6/2016 | Lytle, IV et al. |
| 2016/0175033 | A1 | 6/2016 | Le |
| 2016/0192999 | A1 | 7/2016 | Stulen et al. |
| 2016/0199124 | A1 | 7/2016 | Thomas et al. |
| 2016/0235473 | A1 | 8/2016 | Hagland |
| 2016/0235489 | A1 | 8/2016 | Gombert et al. |
| 2016/0242782 | A1 | 8/2016 | Shelton, IV et al. |
| 2016/0249921 | A1 | 9/2016 | Cappola et al. |
| 2016/0270780 | A1 | 9/2016 | Hall et al. |
| 2016/0287251 | A1 | 10/2016 | Shelton, IV et al. |
| 2016/0287316 | A1 | 10/2016 | Worrell et al. |
| 2016/0296226 | A1 | 10/2016 | Kostrzewski |
| 2016/0317216 | A1 | 11/2016 | Hermes et al. |
| 2016/0338764 | A1 | 11/2016 | Krastins et al. |
| 2016/0345971 | A1 | 12/2016 | Bucciaglia et al. |
| 2016/0374672 | A1 | 12/2016 | Bear et al. |
| 2016/0374673 | A1 | 12/2016 | Stager et al. |
| 2017/0010578 | A1 | 1/2017 | Miyakawa |
| 2017/0042604 | A1 | 2/2017 | McFarland et al. |
| 2017/0055981 | A1 | 3/2017 | Vendely et al. |
| 2017/0056098 | A1 | 3/2017 | Crews et al. |
| 2017/0065331 | A1 | 3/2017 | Mayer et al. |
| 2017/0079710 | A1 | 3/2017 | Deville et al. |
| 2017/0097035 | A1 | 4/2017 | Zimmerman et al. |
| 2017/0105754 | A1 | 4/2017 | Boudreaux et al. |
| 2017/0135746 | A1 | 5/2017 | Tetzlaff et al. |
| 2017/0143335 | A1 | 5/2017 | Gupta et al. |
| 2017/0156788 | A1 | 6/2017 | Johnson et al. |
| 2017/0189028 | A1 | 7/2017 | Aranyi |
| 2017/0202605 | A1 | 7/2017 | Shelton, IV et al. |
| 2017/0231653 | A1 | 8/2017 | Kapadia |
| 2017/0245857 | A1 | 8/2017 | Shelton, IV et al. |
| 2017/0265865 | A1 | 9/2017 | Burbank |
| 2017/0290584 | A1 | 10/2017 | Jasemian et al. |
| 2017/0296172 | A1 | 10/2017 | Harris et al. |
| 2017/0296173 | A1 | 10/2017 | Shelton, IV et al. |
| 2017/0296183 | A1 | 10/2017 | Shelton, IV et al. |
| 2018/0008265 | A1 | 1/2018 | Hatanaka et al. |
| 2018/0021042 | A1 | 1/2018 | Nicholas et al. |
| 2018/0078268 | A1 | 3/2018 | Messerly et al. |
| 2018/0125570 | A1 | 5/2018 | Rioux |
| 2018/0161052 | A1 | 6/2018 | Weir et al. |
| 2018/0168581 | A1 | 6/2018 | Hunter et al. |
| 2018/0168585 | A1 | 6/2018 | Shelton, IV et al. |
| 2018/0168607 | A1 * | 6/2018 | Shelton, IV ..... A61B 17/07207 |
| 2018/0168620 | A1 | 6/2018 | Huang et al. |
| 2018/0168622 | A1 | 6/2018 | Shelton, IV et al. |
| 2018/0168628 | A1 | 6/2018 | Hunter et al. |
| 2018/0168637 | A1 | 6/2018 | Harris et al. |
| 2018/0168641 | A1 | 6/2018 | Harris et al. |
| 2018/0168642 | A1 | 6/2018 | Shelton, IV et al. |
| 2018/0168644 | A1 | 6/2018 | Shelton, IV et al. |
| 2018/0168649 | A1 * | 6/2018 | Shelton, IV ..... A61B 17/07292 |
| 2018/0168650 | A1 | 6/2018 | Shelton, IV et al. |
| 2018/0206844 | A1 | 7/2018 | Harris et al. |
| 2018/0214200 | A1 | 8/2018 | Nanditale et al. |
| 2018/0232951 | A1 | 8/2018 | Alterovitz et al. |
| 2018/0250085 | A1 | 9/2018 | Simi et al. |
| 2018/0296213 | A1 | 10/2018 | Strobl |
| 2018/0310948 | A1 | 11/2018 | Stamm et al. |
| 2018/0317915 | A1 | 11/2018 | McDonald, II |
| 2018/0353186 | A1 | 12/2018 | Mozdzierz et al. |
| 2019/0000454 | A1 | 1/2019 | Swayze et al. |
| 2019/0000525 | A1 | 1/2019 | Messerly et al. |
| 2019/0015124 | A1 | 1/2019 | Williams et al. |
| 2019/0029746 | A1 | 1/2019 | Dudhedia et al. |
| 2019/0059894 | A1 | 2/2019 | Kumada et al. |
| 2019/0076143 | A1 | 3/2019 | Smith |
| 2019/0083086 | A1 | 3/2019 | Klaffenböck et al. |
| 2019/0083819 | A1 | 3/2019 | Mitchell et al. |
| 2019/0099181 | A1 | 4/2019 | Shelton, IV et al. |
| 2019/0125347 | A1 | 5/2019 | Stokes et al. |
| 2019/0133571 | A1 | 5/2019 | Racenet et al. |
| 2019/0142531 | A1 | 5/2019 | Wentworth et al. |
| 2019/0150919 | A1 | 5/2019 | Williams et al. |
| 2019/0192137 | A1 | 6/2019 | Shelton, IV et al. |
| 2019/0201146 | A1 | 7/2019 | Shelton, IV et al. |
| 2019/0231350 | A1 | 8/2019 | Scott et al. |
| 2019/0239881 | A1 | 8/2019 | Laurent et al. |
| 2019/0282233 | A1 | 9/2019 | Burbank et al. |
| 2019/0290374 | A1 | 9/2019 | Ramadorai |
| 2019/0298346 | A1 | 10/2019 | Shelton, IV et al. |
| 2019/0298354 | A1 | 10/2019 | Shelton, IV et al. |
| 2019/0298355 | A1 | 10/2019 | Shelton, IV et al. |
| 2019/0298356 | A1 | 10/2019 | Shelton, IV et al. |
| 2019/0314107 | A1 | 10/2019 | Worrell et al. |
| 2020/0054338 | A1 | 2/2020 | Shen |
| 2020/0205811 | A1 | 7/2020 | Posey et al. |
| 2020/0214706 | A1 | 7/2020 | Vendely et al. |
| 2020/0305872 | A1 | 10/2020 | Weidner et al. |
| 2021/0059670 | A1 | 3/2021 | Overmyer et al. |
| 2021/0153927 | A1 | 5/2021 | Ross et al. |
| 2021/0161529 | A1 | 6/2021 | Wixey |
| 2021/0177412 | A1 | 6/2021 | Wilson et al. |
| 2021/0177495 | A1 | 6/2021 | Ross et al. |
| 2021/0177500 | A1 | 6/2021 | Khalaji |

(56) References Cited

U.S. PATENT DOCUMENTS

| | | | |
|---|---|---|---|
| 2021/0186494 | A1 | 6/2021 | Shelton, IV et al. |
| 2021/0196350 | A1 | 7/2021 | Fiebig et al. |
| 2021/0236119 | A1 | 8/2021 | Chavan et al. |
| 2021/0267596 | A1 | 9/2021 | Fanelli et al. |
| 2021/0290232 | A1 | 9/2021 | Harris et al. |
| 2021/0290233 | A1 | 9/2021 | Shelton, IV et al. |
| 2022/0015823 | A1 | 1/2022 | Wilson et al. |
| 2022/0031346 | A1 | 2/2022 | Parks |
| 2022/0054130 | A1 | 2/2022 | Overmyer et al. |
| 2022/0061836 | A1 | 3/2022 | Parihar et al. |
| 2022/0079585 | A1 | 3/2022 | Egan |
| 2022/0125428 | A1 | 4/2022 | Ragosta et al. |
| 2022/0142642 | A1 | 5/2022 | De et al. |
| 2022/0167985 | A1 | 6/2022 | George et al. |
| 2022/0218344 | A1 | 7/2022 | Leimbach et al. |
| 2022/0296243 | A1 | 9/2022 | Nalagatla et al. |
| 2022/0304691 | A1 | 9/2022 | Fernandes et al. |
| 2022/0346790 | A1 | 11/2022 | Wellman |
| 2022/0378537 | A1 | 12/2022 | Hites et al. |
| 2022/0387027 | A1 | 12/2022 | Shelton, IV et al. |
| 2022/0395270 | A1 | 12/2022 | Patel et al. |
| 2023/0020577 | A1 | 1/2023 | Kerver et al. |
| 2023/0099430 | A1 | 3/2023 | Schings et al. |
| 2023/0101993 | A1 | 3/2023 | Baril et al. |
| 2023/0120209 | A1 | 4/2023 | Parks et al. |
| 2023/0121658 | A1 | 4/2023 | Stokes et al. |
| 2023/0210527 | A1 | 7/2023 | Shelton, IV et al. |
| 2023/0225731 | A1 | 7/2023 | Burbank |
| 2023/0329711 | A1 | 10/2023 | Wixey et al. |
| 2024/0023961 | A1 | 1/2024 | Wixey et al. |
| 2024/0065690 | A1 | 2/2024 | Jasemian et al. |
| 2024/0081824 | A1 | 3/2024 | Hites |
| 2024/0108343 | A1 | 4/2024 | Wixey |
| 2024/0138834 | A1 | 5/2024 | Wellman |
| 2024/0188956 | A1 | 6/2024 | Swayze et al. |
| 2024/0252171 | A1 | 8/2024 | Wixey et al. |
| 2024/0260959 | A1 | 8/2024 | Wixey et al. |
| 2024/0293122 | A1 | 9/2024 | Wixey |
| 2024/0315761 | A1 | 9/2024 | Whitlock et al. |
| 2024/0335194 | A1 | 10/2024 | Patel et al. |
| 2024/0341766 | A1 | 10/2024 | Millman et al. |
| 2024/0350143 | A1 | 10/2024 | Yee et al. |
| 2024/0407782 | A1 | 12/2024 | Patel et al. |
| 2025/0261940 | A1 | 8/2025 | Wixey et al. |
| 2025/0295410 | A1 | 9/2025 | Wellman |
| 2025/0302472 | A1 | 10/2025 | Wixey et al. |
| 2025/0325275 | A1 | 10/2025 | Kerver |
| 2025/0331857 | A1 | 10/2025 | Wixey et al. |
| 2025/0359870 | A1 | 11/2025 | Yee et al. |

FOREIGN PATENT DOCUMENTS

| | | | | | |
|---|---|---|---|---|---|
| CN | 104042275 | A | | 9/2014 | |
| CN | 105007836 | A | | 10/2015 | |
| CN | 105769331 | A | | 7/2016 | |
| CN | 106232026 | A | | 12/2016 | |
| CN | 106491203 | A | | 3/2017 | |
| CN | 107920819 | A | | 4/2018 | |
| CN | 108024809 | A | | 5/2018 | |
| CN | 112165909 | A | | 1/2021 | |
| DE | 694747 | C | | 8/1940 | |
| DE | 3724525 | C1 | | 5/1988 | |
| DE | 102012103503 | A1 | | 10/2013 | |
| EP | 0277532 | B1 | | 8/1990 | |
| EP | 0469396 | A1 | | 2/1992 | |
| EP | 0277529 | B1 | | 4/1993 | |
| EP | 0641546 | A1 | | 3/1995 | |
| EP | 0986336 | A1 | | 3/2000 | |
| EP | 1090592 | A1 | | 4/2001 | |
| EP | 1479348 | A1 | | 11/2004 | |
| EP | 1728473 | A1 | | 12/2006 | |
| EP | 1479346 | B1 | | 1/2007 | |
| EP | 1621141 | B1 | | 7/2007 | |
| EP | 2374419 | A2 | | 10/2011 | |
| EP | 1316290 | B1 | | 2/2012 | |
| EP | 2517639 | A1 | | 10/2012 | |
| EP | 2540231 | A2 | | 1/2013 | |
| EP | 1754445 | B1 | | 10/2013 | |
| EP | 2774548 | A2 | * | 9/2014 | ....... A61B 17/07207 |
| EP | 2777529 | A1 | | 9/2014 | |
| EP | 2777530 | A1 | | 9/2014 | |
| EP | 2777532 | A2 | | 9/2014 | |
| EP | 2777535 | A1 | | 9/2014 | |
| EP | 2779921 | A2 | | 9/2014 | |
| EP | 2932918 | A1 | | 10/2015 | |
| EP | 2944275 | A2 | | 11/2015 | |
| EP | 2992834 | A1 | | 3/2016 | |
| EP | 2992849 | A1 | | 3/2016 | |
| EP | 3000408 | A2 | | 3/2016 | |
| EP | 3120780 | A2 | | 1/2017 | |
| EP | 3135225 | A2 | | 3/2017 | |
| EP | 3158947 | A1 | | 4/2017 | |
| EP | 3173029 | A1 | | 5/2017 | |
| EP | 3205291 | A1 | | 8/2017 | |
| EP | 3338703 | A1 | | 6/2018 | |
| EP | 2992834 | B1 | | 12/2018 | |
| EP | 3498190 | A1 | | 6/2019 | |
| EP | 3756567 | A1 | | 12/2020 | |
| FR | 2828952 | B1 | | 12/2005 | |
| JP | S5794132 | A | | 6/1982 | |
| JP | 2001170069 | A | | 6/2001 | |
| JP | 5301166 | B2 | | 9/2013 | |
| JP | 2014530653 | A | | 11/2014 | |
| JP | 2016508792 | A | | 3/2016 | |
| JP | 2016513570 | A | | 5/2016 | |
| JP | 2017500146 | A | | 1/2017 | |
| JP | 2017513564 | A | | 6/2017 | |
| JP | 2017527396 | A | | 9/2017 | |
| JP | 6411461 | B2 | | 10/2018 | |
| JP | 2019141659 | A | | 8/2019 | |
| KR | 20170060064 | | * | 5/2017 | ....... A61B 217/0725 |
| SU | 405234 | A1 | | 9/1975 | |
| SU | 886900 | A1 | | 12/1981 | |
| SU | 1333319 | A2 | | 8/1987 | |
| SU | 1442191 | A1 | | 12/1988 | |
| SU | 1459659 | A1 | | 2/1989 | |
| WO | WO-8602254 | A1 | | 4/1986 | |
| WO | WO-9005489 | A1 | | 5/1990 | |
| WO | WO-9734533 | A1 | | 9/1997 | |
| WO | WO-03094743 | A1 | | 11/2003 | |
| WO | WO-03094746 | A1 | | 11/2003 | |
| WO | WO-03094747 | A1 | | 11/2003 | |
| WO | WO-2004020859 | A1 | | 3/2004 | |
| WO | WO-2009112802 | A1 | | 9/2009 | |
| WO | WO-2012142872 | A1 | | 10/2012 | |
| WO | WO-2014106275 | A1 | | 7/2014 | |
| WO | WO-2016073538 | A1 | | 5/2016 | |
| WO | WO-2017026141 | A1 | | 2/2017 | |
| WO | WO-2017034803 | A2 | | 3/2017 | |
| WO | WO-2017156070 | A1 | | 9/2017 | |
| WO | WO-2017214243 | A1 | | 12/2017 | |
| WO | WO-2018005750 | A1 | | 1/2018 | |
| WO | WO-2018071497 | A1 | | 4/2018 | |
| WO | WO-2018118402 | A1 | | 6/2018 | |
| WO | WO-2019090047 | A1 | | 5/2019 | |
| WO | WO-2020081960 | A1 | | 4/2020 | |
| WO | WO-2020131685 | A1 | | 6/2020 | |
| WO | WO-2020131692 | A1 | | 6/2020 | |
| WO | WO-2022150215 | A1 | | 7/2022 | |
| WO | WO-2022200951 | A1 | | 9/2022 | |

OTHER PUBLICATIONS

Jaggi A., "8 mm SureForm 30 Curved-Tip Stapler, 8 mm SureForm 30 Stapler, SureForm 30 Reloads," U.S Food & Drug Administration, Dec. 2021, 11 pages. Retrieved from the internet URL:https://www.sages.org/publications/tavac/8-mm-sureform-30-staplers-and-reloads/.

International Search Report and Written Opinion for Application No. PCT/US2024/026826, mailed Jul. 26, 2024, 15 pages.

Anonymous: "Slip Joint Pliers—Wikipedia," Sep. 2017, 1 Pages. Retrieved from internet URL:https://en.wikipedia.org/w/index.php?tilte=split_joint_pliers&oldid=801407143.

(56) References Cited

OTHER PUBLICATIONS

European Search Report (Corrected version) for Application No. EP19750317.0, mailed on Mar. 28, 2022, 26 pages.
Extended European Search Report for Application No. EP18823002.3 mailed on Mar. 5, 2021, 11 pages.
Extended European Search Report for Application No. EP19757451.0, mailed on May 19, 2022, 16 pages.
Extended European Search Report for Application No. EP19898247.2, mailed on Jan. 10, 2023, 12 pages.
Extended European Search Report for Application No. EP19900059.7, mailed on Dec. 5, 2022, 10 pages.
Extended European Search Report for Application No. EP20790773.4, mailed on Nov. 29, 2022, 09 pages.
Extended European Search Report for Application No. EP20815112.6, mailed on Jan. 5, 2023, 11 pages.
Extended European Search Report for Application No. EP20875978.7, mailed on Jan. 31, 2024, 26 pages.
Extended European Search Report for Application No. EP24155564.8, mailed on Jul. 8, 2024, 12 pages.
Field Application Note—Journal Bearings, Retrieved from Wayback Machine URL: https://web.archive.org/web/20100110095051/ http://www.reliabilitydirect.com/appnotes/jb.html, on Mar. 12, 2024, 04 pages.
International Preliminary Report on Patentability for Application No. PCT/US2019/017646, mailed on Aug. 27, 2020, 10 pages.
International Preliminary Report on Patentability for Application No. PCT/US2019/019501, mailed Sep. 3, 2020, 7 pages.
International Search Report and Written Opinion for Application No. PCT/US19/17646, mailed on Apr. 16, 2019, 11 pages.
International Search Report and Written Opinion for Application No. PCT/US2016/059527, mailed on Feb. 16, 2017, 13 pages.
International Search Report and Written Opinion for Application No. PCT/US2018/039912, mailed on Oct. 12, 2018, 15 pages.
International Search Report and Written Opinion for Application No. PCT/US2019/019501, mailed May 9, 2019, 8 pages.
International Search Report and Written Opinion for Application No. PCT/US2019/056979, mailed Dec. 18, 2019, 8 pages.
International Search Report and Written Opinion for Application No. PCT/US2019/062344, mailed Mar. 23, 2020, 17 pages.
International Search Report and Written Opinion for Application No. PCT/US2019/062768, mailed Mar. 9, 2020, 15 pages.
International Search Report and Written Opinion for Application No. PCT/US2019/064861, mailed Mar. 30, 2020, 18 pages.
International Search Report and Written Opinion for Application No. PCT/US2019/066513, mailed Apr. 21, 2020, 8 pages.
International Search Report and Written Opinion for Application No. PCT/US2019/066530, mailed Apr. 21, 2020, 8 pages.
International Search Report and Written Opinion for Application No. PCT/US202 1/065544 mailed Jun. 2, 2022, 21 pages.
International Search Report and Written Opinion for Application No. PCT/US2020/020672, mailed Jun. 29, 2020, 10 pages.
International Search Report and Written Opinion for Application No. PCT/US2020/025655, mailed Jul. 22, 2020, 8 pages.
International Search Report and Written Opinion for Application No. PCT/US2020/033481, mailed Sep. 3, 2020, 22 pages.
International Search Report and Written Opinion for Application No. PCT/US2020/054568, mailed Jan. 29, 2021, 13 pages.
International Search Report and Written Opinion for Application No. PCT/US2021/012284 mailed May 6, 2021,23 pages.
International Search Report and Written Opinion for Application No. PCT/US2021/065308, mailed Apr. 21, 2022. 13 pages.
Nicholson, C., et al., "Plane Bearings," ESC Report, BSA Educational Services Committee, Oct. 1994, vol. 5(1), 02 pages.
Partial European Search Report for Application No. EP19757451.0, mailed on Feb. 2, 2022, 12 pages.
Supplementary European Search Report for Application No. EP19873128.3, mailed on Jun. 22, 2022, 7 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Article Name, found online xx/xx/xxxx at amazon.com (store brand base url). Reference dated xx/xx/xxxx. Retrieved from https://web.archive.org/web/20140704001512/ http://www.adorama.com/FSSTC10.html.
"Echelon Gripping Surface Technology Reloads," Ethicon, 2023, 1 Page. Retrieved from online URL:[https://web.archive.Org/web/20230328053734/https://www.jnjmedtech.com/en-US/product/ echelon-gripping-surfacetechnology reloads].
"Itoya 3/8" Switch Heavy Duty Disposable Staple Cassettes, Adorama, 2014, 1 page. Retrieved from Online URL: [https://web.archive.Org/web/20140704001512/ http://www.adorama.com/FSSTC10.html].
"Linear Cutter Stapler," Fengh Europe, 2024, 1 Page. Retrieved from Online URL: [https://web.archive.org/web/20240223162323/https://fenghmedical.nl/product/linear-cutter-stapler/].
McKesson Staple Loading Unit, found online Dec. 30, 2025 at https://mms.mckesson.com Reference dated Apr. 15, 2021. Retrieved from https://web.archive.Org/web/20210415093906/https://mms.mckesson.com/product/453729/J-J-Healthcare-Systems-6R45B.

* cited by examiner

SURGICAL INSTRUMENT WITH ADJUSTABLE JAWS

CROSS-REFERENCE TO RELATED APPLICATIONS

This application is a continuation of U.S. patent application Ser. No. 17/764,918 filed Mar. 29, 2022, which is a is the National Stage of International Application No. PCT/US2020/054568 filed Oct. 7, 2020, which claims benefit of U.S. Provisional Application Ser. No. 62/916,860, filed Oct. 18, 2019 and U.S. Provisional Application Ser. No. 62/916,864, filed Oct. 18, 2019, the entire disclosures of which are incorporated herein by reference for all purposes.

BACKGROUND

The field of the present disclosure relates to medical instruments, and more particularly to tissue sealing instruments for use in surgeries. Even more particularly, the present disclosure relates to a surgical stapling instrument having adjustable jaws that enable multiple settings between the jaws to reduce the cross-sectional dimensions of the surgical instrument and/or to allow the surgeon to use different staple cartridges without having to change surgical instruments.

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI™ system commercialized by Intuitive Surgical, Inc. of Sunnyvale, Calif.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. No. 7,594,912 (filed Sep. 30, 2004), U.S. Pat. No. 6,758,843 (filed Apr. 26, 2002), U.S. Pat. No. 6,246,200 (filed Aug. 3, 1999), and U.S. Pat. No. 5,800,423 (filed Jul. 20, 1995), the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. No. 6,702,805 (filed Nov. 9, 2000), U.S. Pat. No. 6,676,669 (filed Jan. 16, 2002), U.S. Pat. No. 5,855,583 (filed Nov. 22, 1996), U.S. Pat. No. 5,808,665 (filed Sep. 9, 1996), U.S. Pat. No. 5,445,166 (filed Apr. 6, 1994), and U.S. Pat. No. 5,184,601 (filed Aug. 5, 1991), the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical clamping and cutting instruments (e.g., linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting devices, including known surgical staplers, have opposing jaws that clamp tissue and an articulated knife to cut the clamped tissue.

Surgical clamping and cutting instruments are often deployed into restrictive body cavities (e.g., through a cannula to inside the pelvis). Accordingly, it is desirable for the surgical clamping and cutting instrument to be both compact and maneuverable for best access to and visibility of the surgical site. Known surgical clamping and cutting instruments, however, may fail to be both compact and maneuverable. For example, known surgical staplers may lack maneuverability with respect to multiple degrees of freedom (e.g., Roll, Pitch, and Yaw) and associated desired ranges of motion.

Conventional surgical clamping and cutting instruments typically include an end effector with a fixed jaw and a movable jaw that can be opened and closed relative to the fixed jaw. A staple cartridge is often designed to fit within the movable jaw of the end effector. The staple cartridge contains multiple rows of staple assemblies that each includes a staple and a staple driver, sometimes referred to as a staple pusher. The staple pusher holds the staple in place prior to use, and then drives the staple into tissue when the instrument is actuated. Prior to actuation of the staples, the jaws are in a "closed" position around the tissue. In this closed position, the jaws are typically parallel to each other such that the distance between the upper and lower jaws is a fixed dimension along the length of the jaws. This parallel tissue gap between the jaws places the jaws in close cooperative alignment for clamping, sealing and/or holding the tissue in place prior to stapling.

The requisite tissue gap between the closed jaws in conventional instruments essentially becomes an air gap when the instrument is being introduced and retracted through cannulas, or when the instrument is being maneuvered within the patient's body cavity. This air gap is empty space that is fundamentally lost height in the vertical stack-up of the device, effectively limiting the ability of the designer to reduce the overall size of the instrument or to increase the height of the staples for an instrument of a given size.

Depending on the clinical requirements of the procedure and/or the surgeon's preference, different types of staple cartridges may be desired. For example, certain staple cartridges have taller staples than others in the event that, for example, a stronger tissue seal is required. In other cases, shorter staples may be desired to avoid damage to collateral tissue in tightly confined spaces.

Unfortunately, most conventional staple instruments are only designed to accommodate one particular size of staple cartridge. This is because they are designed with a "fixed jaw" distance such that when the jaws are set to parallel in the closed position, the tissue gap between the jaws is maintained as a fixed dimension in order to provide sufficient clearance for clamping tissue in place prior to stapling. Thus, a surgical instrument with a fixed jaw distance designed for use with, for example, a staple cartridge having relatively short staples cannot be used with a staple cartridge having taller staples without reducing the tissue gap between the jaws (or completely removing the gap so that there is zero or negative clearance between the jaws), thereby compromising the surgical procedure.

Accordingly, while the new telesurgical systems and devices have proven highly effective and advantageous, still further improvements would be desirable. In general, it would be desirable to provide improved surgical instruments that are more adaptable, as well as more compact and maneuverable, to enhance the efficiency and ease of use of minimally invasive systems. More specifically, it would be beneficial to provide surgical stapling instruments capable of accommodating staple cartridges of different sizes to reduce the cost, and/or enhance the efficiency, of surgical procedures. In addition, it would be desirable to reduce the size of the air gap between the jaws of surgical instruments when the jaws are being moved to access the tissue site, while still retaining the requisite jaw clearance to clamp tissue during actuation of the device.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure provides a surgical instrument, such as a tissue sealing instrument, with an end effector having a first jaw and a second jaw configured to move relative to each other from an open position to a closed position. The first and second jaws define a gap therebetween in the closed position. In one aspect, the jaws are also movable relative to each other in the closed position to reduce a thickness of at least one portion of the gap. The present invention allows the jaws to be moved closer together to reduce the overall size of the instrument when, for example, the instrument is introduced and retracted through a cannula or other percutaneous penetration in the patient, or when the instrument is being maneuvered within a body cavity. In turn, the jaws can be moved away from each other to create a tissue gap sufficient for clamping, sealing and/or stapling tissue. This design eliminates at least a portion of the tissue/air gap during access of the target site within the patient, thereby reducing the cross-sectional dimension of the end effector relative to conventional devices and allowing for a more compact and maneuverable surgical instrument.

In another aspect, the surgical instrument may also have multiple settings for use with different staple cartridges, while still maintaining a fixed dimension between the two jaws for clamping, stapling and/or sealing tissue, providing a more adaptable surgical instrument that allows the surgeon to use different staple cartridges without having to change surgical instruments.

In one embodiment, the first and second jaws are movable between a first or "closed" position wherein the jaws are substantially parallel to each other and the gap defines a first thickness between the first and second jaws, and a second or "overclosed" position wherein at least a portion of the gap defines a second thickness that is less than the first distance. Thus, at least one portion of the jaws are closer to each other in the second position, thereby reducing the thickness of the gap. This allows the jaws to collapse at least a portion of the air gap to allow the end effector to, for example, pass through a fixed cannula diameter and expand the gap during surgical operation to allow for sufficient clearance between the jaws to clamp, seal and/or staple tissue.

In one aspect of the invention, the second jaw is pivotally coupled to the first fixed jaw to open and close the jaws relative to each other. In the closed position, the first and second jaws are substantially parallel to each other. The second jaw is preferably configured to pivot in both directions from this substantially parallel position. Pivoting the second jaw away from the first jaw opens the jaws, allowing the surgeon to place them around the target tissue. Pivoting the second jaw closer to the first jaw from the parallel position brings the distal portion of the second jaw into the overclosed position, which reduces the distance between the distal portions of the jaws, thereby reducing the thickness of at least the distal portion of the gap. In an exemplary embodiment, the second jaw defines an angle in the overclosed position between about 0.4 to about 2.0 degrees, preferably between about 0.5 to about 1.0 degrees, and more preferably about 0.55 with respect to the longitudinal axis of the end effector.

In certain embodiments, a proximal portion of the second jaw has a recess, or material cut-out, extending around the outer surface of the second jaw opposite the first jaw such that the end effector has a small cross-sectional diameter at the proximal portion than the distal portion in the closed position. Thus, when the distal portion of the second jaw has pivoted towards the first jaw into the overclosed position, the diameter of this distal portion substantially matches the diameter of the proximal portion, thereby reducing the overall cross-sectional dimensions of the end effector. Alternatively, the entire lower surface of the second jaw may be inclined to substantially match the angle made between the second jaw and the longitudinal axis in the overclosed position. In certain embodiments, the second jaw may also have an inclined upper surface opposite the first jaw on at least the distal portion of the second jaw. This inclined upper surface provides more clearance space for the distal portion of the second jaw as it is moved closer to the first jaw in the second position.

In one embodiment, the surgical instrument comprises a hinge that pivotally couples the first and second jaws to each other. The hinge is preferably biased towards the open position and configured to pivot into the overclosed position upon the application of force to the distal end portion of the first jaw. In use, an operator, such as a surgeon, can hold the jaws together in the overclosed position before inserting the end effector into a cannula or other percutaneous penetration in the patient. Once the end effector has passed through the cannula and into the patient's body cavity, the jaws will automatically pivot back into the open position. Upon withdrawal of the instrument, the inner surface of the cannula will provide sufficient force to the end effector to pivot the second jaw into the overclosed position such that the device has a small enough cross-sectional area to retract proximally through the cannula.

In an alternative embodiment, the end effector comprises a locking mechanism for locking the jaws in either or both of the closed or overclosed positions. The locking mechanism may be coupled to an actuator, camming surface, gear or other suitable mechanism in the surgical instrument that can be controlled by the operator, or that automatically locks/unlocks the jaws during operation. In one such embodiment, the jaws may be locked in the overclosed position so that the surgeon can more easily maneuver the device within a patient's body cavity to access the target site.

In another aspect of the invention, the surgical instrument includes an actuator coupled to the end effector and configured to move one or both of the jaws between a first position wherein the jaws are substantially parallel and define a gap therebetween, and a second position, wherein the jaws are closer together such that the thickness of at least one portion of the gap is reduced. In one embodiment, the actuator comprises a rotatable drive member coupled to one of the first and second jaws. The rotatable drive member is configured to rotate and engage one of the jaws, causing translation of the first or second jaw in a direction that reduces or increases the gap therebetween. In an alternative embodiment, the actuator comprises a cable drive coupled to one or both of the first and second jaws and configured to translate the first or second jaw towards and away from each other.

In another aspect of the invention, the surgical instrument includes a staple cartridge coupled to one of the first and second jaws and housing a plurality of staples. The surgical instrument further comprises a drive member configured to translate distally through a channel in the end effector to engage the staples and drive them into tissue when the instrument is actuated. The drive member and/or one of the first and second jaws include camming surface(s) sized and configured to engage with each other when the drive member is translated through the end effector. The camming surface(s) are configured to cause translation of at least one of the jaws in a direction substantially perpendicular to the longitudinal axis upon distal advancement of the drive member. Thus, the drive member automatically moves the jaws towards and/or away from each other to reduce or increase the thickness of the tissue gap therebetween.

In yet another aspect of the invention, the surgical instrument further includes one or more locking mechanisms for locking the first and second jaws in the closed and/or overclosed positions. In one embodiment, the locking mechanism is coupled to the drive member and configured to engage the drive member upon distal and/or proximal translation of the drive member through the end effector. In an exemplary embodiment, the locking mechanism comprises a locking member biased by a spring and coupled to one of the first and second jaws. The locking member may be biased towards the locked or unlocked configuration and may also be coupled to the drive member such that translation of the drive member caused the locking member to unlock or lock.

In another aspect of the invention, the surgical instrument further includes an actuation mechanism in contact with the central portion of the drive member. The actuation mechanism is configured to advance the drive member distally through the end effector and, in some cases, retract the drive member proximally through the end effector. In an exemplary embodiment, the actuator includes a control device of a robotic telesurgical system that may, for example, allow for mechanical actuation and control of the surgical instrument to perform a variety of functions, such as grasping a blood vessel, dissecting tissue, or the like, in response to manipulation of master input devices located remotely from the surgical instrument.

In yet another aspect of the invention, a surgical instrument comprises a drive member and an end effector comprising a first jaw rotatably coupled to a second jaw. At least one of the first jaw and the second jaw is movable between a first configuration and a second configuration. In the first configuration, a distance separating a distal end of the first jaw from a distal end of the second jaw is less than a distance separating a proximal end of the first jaw from a proximal end of the second jaw. In the second configuration, the distance separating the distal end of the first jaw from the distal end of the second jaw is approximately equal to the distance separating the proximal end of the first jaw from the proximal end of the second jaw.

In one embodiment, the first jaw defines a first longitudinal slot configured to accommodate a first lateral projection of the drive member, and the second jaw defines a second longitudinal slot configured to accommodate a second lateral projection of the drive member. The height of the distal end of the second jaw is preferably greater than a height of the proximal end of the second jaw.

In certain embodiments, a distance separating an outer surface of the second jaw from a tissue-contacting surface of the second jaw at the distal end of the second jaw is greater than a distance separating the outer surface of the second jaw from the tissue-contacting surface of the second jaw at the proximal end of the second jaw. A length of the first longitudinal slot is greater than a length of the second longitudinal slot. The first longitudinal slot extends from the proximal end of the first jaw to the distal end of the first jaw. The second longitudinal slot extends from (i) a midway position between the proximal end of the second jaw and the distal end of the second jaw, to (ii) the distal end of the second jaw.

In another aspect of the invention, the present disclosure provides a surgical instrument, such as a tissue sealing instrument, with an end effector having a longitudinal axis and comprising first and second jaws movable relative to each other between open and closed positions. The instrument further includes a coupling member for removably coupling at least two different staple cartridges to the second jaw (at separate times), and a drive member configured to translate distally and retract proximally through the staple cartridge. The drive member and the jaws are configured to cooperate with each other to position an upper surface of each of the staple cartridges at a fixed distance from the first jaw when each of the staple cartridges are separately coupled to the second jaw and the jaws are in the closed position.

The first and second staple cartridges may have different heights relative to the longitudinal axis of the end effector (e.g., taller or shorter staples). In such case, the drive member and the jaws cooperate with each other such that the upper surface of each of the staple cartridges remains at the same fixed distance from the first jaw regardless of the height of each of the staple cartridges. This provides a surgical instrument with multiple settings for use with different staple cartridges, while still maintaining a fixed dimension between the two jaws for clamping, stapling and/or sealing tissue. A more adaptable surgical instrument allows the surgeon to use staple cartridges with different heights (e.g., taller or shorter staples) without having to change surgical instruments. In certain embodiments, the jaws and drive member may have more than two settings to accommodate more than two different staple cartridges, e.g., three or more staple cartridges each having a different height.

In one embodiment, the surgical instrument further comprises at least first and second channels in the end effector configured to receive at least a portion of the drive member as the drive member translates longitudinally through the end effector. The first and second channels are substantially parallel to each other and spaced from each other in a direction substantially perpendicular to the longitudinal axis of the end effector. The drive member is configured for translation through the first channel when the first staple cartridge is coupled to the second jaw and through the second channel when the second staple cartridge is coupled to the second jaw. In an exemplary embodiment, the first and second channels are formed within the first jaw and the drive member is fixed in the perpendicular direction relative to the second jaw and the staple cartridges when they are coupled thereto. Alternatively, the first and second channels may be formed in the second jaw and/or the staple cartridges and the drive member fixed relative to the first jaw. In both cases, the drive member is positioned such that the tissue gap between the jaws in the closed position will be substantially the same for both staple cartridges as the drive member is translated through the end effector. This allows the end effector to accommodate two staple cartridges with different heights without changing the thickness of the tissue gap between the jaws.

The surgical instrument may further comprise an actuator for aligning the drive member with either the first or second channel and thereby moving the second jaw into either a first or second position relative to the first jaw. In one embodiment, the actuator comprises a rotatable drive member coupled to one of the first and second jaws. The rotatable drive member is configured to rotate and engage the drive member, causing vertical translation of the drive member between the first and second positions. In an alternative embodiment, the actuator comprises a cable drive coupled to the drive member and/or one of the first and second jaws. The cable drive is configured to translate the drive member vertically relative to one or both of the jaws between the first and second positions. Other actuators may be used with the present invention, such as a push rod, wedge or other camming surface, screw rod, rack-pinion or other suitable mechanism for translating the drive member between the first and second positions. The actuator may be controlled with a user interface on a proximal handle of the surgical instrument or through a robotic control device suitably coupled to the instrument. Alternatively, the staple cartridges may each be sized such that, when they are loaded into the second jaw, the drive member automatically aligns with one of the first and second channels (depending on the size of the staple cartridge, or the height of the staples therein).

In another embodiment, the end effector comprises a single channel and the drive member comprises an elongate body with first and second projections extending therefrom. The first and second projections are spaced from each other in a direction substantially perpendicular to the longitudinal axis of the end effector. The first and second projections are removably couplable to the staple cartridges in the second jaw and configured such that coupling the stable cartridge with the first projection of the drive member situates the drive member in a first perpendicular position relative to the first jaw. Coupling the staple cartridge with the second projection of the drive member situates the drive member in a second perpendicular position relative to the first jaw. Alternatively, the drive member may comprise a single projection that is movable relative to the elongate body to adjust the height at which the drive member is aligned with the channel in the end effector.

In another aspect of the invention, a surgical instrument comprises an end effector having first and second jaws configured to move relative to each other between open and closed positions. The first and second jaws define a substantially parallel gap therebetween in the closed position. One of the first and second jaws is movable in a direction substantially parallel to the longitudinal axis of the end effector to change the thickness of this gap. In this embodiment, the jaws can be moved closer together to reduce the overall size of the instrument when, for example, the instrument is introduced and retracted through a cannula or other percutaneous penetration in the patient, or when the instrument is being maneuvered within a body cavity. In turn, the jaws can be moved away from each other to create a tissue gap sufficient for clamping, sealing and/or stapling tissue. This design eliminates at least a portion of the tissue/air gap during access of the target site within the patient, thereby reducing the cross-sectional dimension of the end effector relative to conventional devices and allowing for a more compact and maneuverable surgical instrument.

In certain embodiments, the surgical instrument includes a staple cartridge coupled to one of the first and second jaws and housing a plurality of staples. The surgical instrument further comprises a drive member configured to translate distally and retract proximally through a channel in the end effector to engage the staples and drive them into tissue when the instrument is actuated. In one such embodiment, the end effector comprises first and second channels extending in a longitudinal direction and sized to receive at least a portion of the drive member. The first and second channels are substantially parallel with each other and spaced in a direction substantially perpendicular to the longitudinal axis. The drive member is configured to translate through either the first or the second channel upon actuation of the instrument. The drive member is coupled to one of the first and second jaws and is preferably movable in a perpendicular direction between the first and second channels. In this way, the drive member may be aligned with either the first or second channel depending on the desired tissue gap between the jaws.

In another aspect of the invention, the surgical instrument includes an actuator coupled to the end effector and configured to move one or both of the jaws between a first position wherein the jaws are substantially parallel and define a gap therebetween, and a second position, wherein the jaws are closer together such that the thickness of at least one portion of the gap is reduced. The surgical instrument may further include one or more locking mechanisms for locking the first and second jaws in the first and/or second positions. In one embodiment, the locking mechanism is coupled to the drive member and configured to engage the drive member upon distal and/or proximal translation of the drive member through the end effector.

In another aspect of the invention, the surgical instrument further includes an actuation mechanism in contact with the central portion of the drive member. The actuation mechanism is configured to advance the drive member distally through the end effector and to retract the drive member proximally through the end effector. In an exemplary embodiment, the actuator includes a control device of a robotic telesurgical system that may, for example, allow for mechanical actuation and control of the surgical instrument to perform a variety of functions, such as grasping a blood vessel, dissecting tissue, or the like, in response to manipulation of master input devices located remotely from the surgical instrument.

In yet another aspect of the invention, a surgical instrument set comprises a surgical instrument having an end effector with first and second jaws configured to pivot relative to each other between open and closed positions such that the jaws define a substantially longitudinal gap in the closed position. The surgical instrument set further includes first and second staple cartridges removably couplable to the second jaw of the end effector and each comprising a plurality of staples. The first and second staple cartridges each have a height in a direction transverse to the longitudinal axis of the end effector. The height of the first staple cartridge is greater than the height of the second staple cartridge. The end effector is configured such that the thickness of the gap is substantially the same when either the first or second staple cartridge is coupled to the second jaw.

In an exemplary embodiment, the staple cartridges each comprise a channel for receiving a drive member of the surgical instrument. The channels are each spaced from the upper surfaces of the staple cartridges such that, when the drive member is translated longitudinally through the channels, the gap between the upper surface of the staple cartridge and the lower surface of the first jaw is substantially the same. Thus, if the first staple cartridge is taller than the second staple cartridge, the channel in the first staple cartridge is positioned higher than the channel in the second staple cartridge relative to the bottom surface of the staple cartridges. This ensures that the thickness of the gap between the jaws will remain the same regardless of the height of the individual staple cartridge.

In another aspect of the invention, a surgical instrument comprises a drive member having first and second lateral projections and an end effector comprising a first jaw rotatably coupled to a second jaw. The first jaw defines first and second longitudinal slots each configured to accommodate the first lateral projection of the drive member, wherein the second jaw defines a third longitudinal slot configured to accommodate the second lateral projection of the drive member. During a first operational mode, the first lateral projection travels within the first longitudinal slot of the first jaw. During a second operational mode, the first lateral projection travels within the second longitudinal slot of the first jaw.

The surgical instrument preferably further comprises an actuator configured to switch between the first operational mode and the second operational mode. In one embodiment, the actuator comprises a camming surface configured to cooperate with the first lateral projection of the drive member such that distal translation of the drive member moves the lateral projection from the first longitudinal slot to the second longitudinal slot. In another embodiment, the actuator comprises first and second coupling members pivotally coupled to each other and configured to move the first lateral projection of the drive member between the first and second longitudinal slots. In yet another embodiment, the actuator comprises a rotatable drive member pivotally coupled to the end effector and configured to move the first lateral projection of the drive member between the first and second longitudinal slots. In another embodiment, the actuator comprises a cam mover plate having an opening defining an inclined camming surface and an actuating mechanism coupled to the cam move plate and configured to move the first lateral projection of the drive member between the first and second longitudinal slots.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description serve to explain the principles of the disclosure.

DETAILED DESCRIPTION

Figure 1:
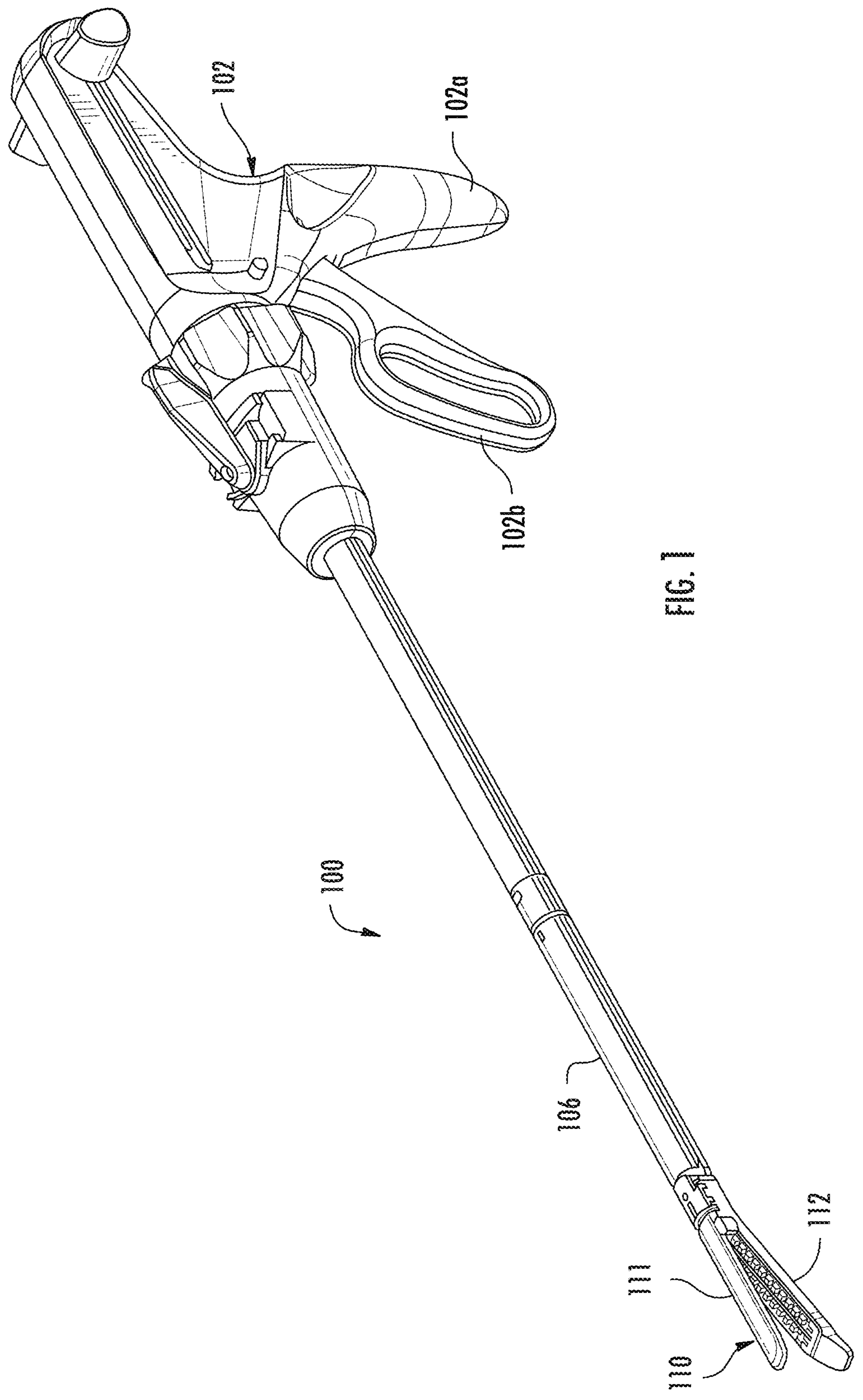
FIG. 1 illustrates a perspective view of an illustrative surgical instrument having an end effector mounted to an elongated shaft.

This description and the accompanying drawings illustrate exemplary embodiments and should not be taken as limiting, with the claims defining the scope of the present disclosure, including equivalents. Various mechanical, compositional, structural, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

While the following disclosure is presented with respect to a linear surgical stapler where staples are sequentially fired, it should be understood that the features of the presently described surgical instruments may be readily adapted for use in any type of surgical clamping, cutting, or sealing instruments, whether or not the surgical clamping and cutting instrument applies a fastener. For example, the presently described drive member and actuation mechanism may be employed in an electrosurgical instrument wherein the jaws include electrodes for applying energy to tissue to treat (e.g., cauterize, ablate, fuse, or cut) the tissue. The surgical clamping and cutting instrument may be a minimally invasive (e.g., laparoscopic) instrument or an instrument used for open surgery.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

While several embodiments of an illustrative surgical instrument are described below and shown in the drawings, it is not intended that the disclosure be limited to these particular instruments. The embodiments of the present disclosure may be incorporated into the a variety of different surgical instruments, such as those described in commonly-assigned, co-pending U.S. Provisional Patent Application Nos. 62/947,307, 62/947,263 and 62/961,504; U.S. patent application Ser. Nos. 16/205,128, 16/678,405 and 16/904,482; and International Patent Nos. PCT/US2019/107646, PCT/US2019/019501, PCT/US2019/062344, PCT/US2019/064861, PCT/US2019/062768, PCT/2020/025655, PCT/US2020/056979, PCT/2019/066513, PCT/US2020/020672 and PCT/US2019/066530 and PCT/US2020/033481, the complete disclosures of which are incorporated by reference herein in their entirety for all purposes as if copied and pasted herein.

FIG. 1 is a perspective view of an illustrative surgical instrument 100 in accordance with certain embodiments of the present disclosure having a handle assembly 102, and an end effector 110 mounted on an elongated shaft 106 of the surgical stapling instrument 100. End effector 110 includes a first jaw 111 and a second jaw 112. Handle assembly 102 includes a stationary handle 102*a* and a moveable handle 102*b*, which serves as an actuator for surgical instrument 100.

In certain embodiments, handle assembly 102 may include input couplers (not shown) instead of, or in addition to, the stationary and movable handles. The input couplers provide a mechanical coupling between the drive tendons or cables of the instrument and motorized axes of the mechanical interface of a drive system. The input couplers may interface with, and be driven by, corresponding output couplers (not shown) of a telesurgical surgery system, such as the system disclosed in U.S Pub. No. 2014/0183244A1, the entire disclosure of which is incorporated by reference herein for all purposes. The input couplers are drivingly coupled with one or more input members (not shown) that are disposed within the instrument shaft 106 and end effector 110. Suitable input couplers can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety for all purposes. Further details of known input couplers and surgical systems are described, for example, in U.S. Pat. Nos. 8,597,280, 7,048,745, and 10,016,244. Each of these patents is hereby incorporated by reference in its entirety for all purposes.

Actuation mechanisms of surgical instrument 100 may employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties for all purposes. While described herein with respect to an instrument configured for use with a robotic surgical system, it should be understood that the wrist assemblies described herein may be incorporated into manually actuated instruments, electro-mechanical powered instruments, or instruments actuated in any other way.

Figure 1A:
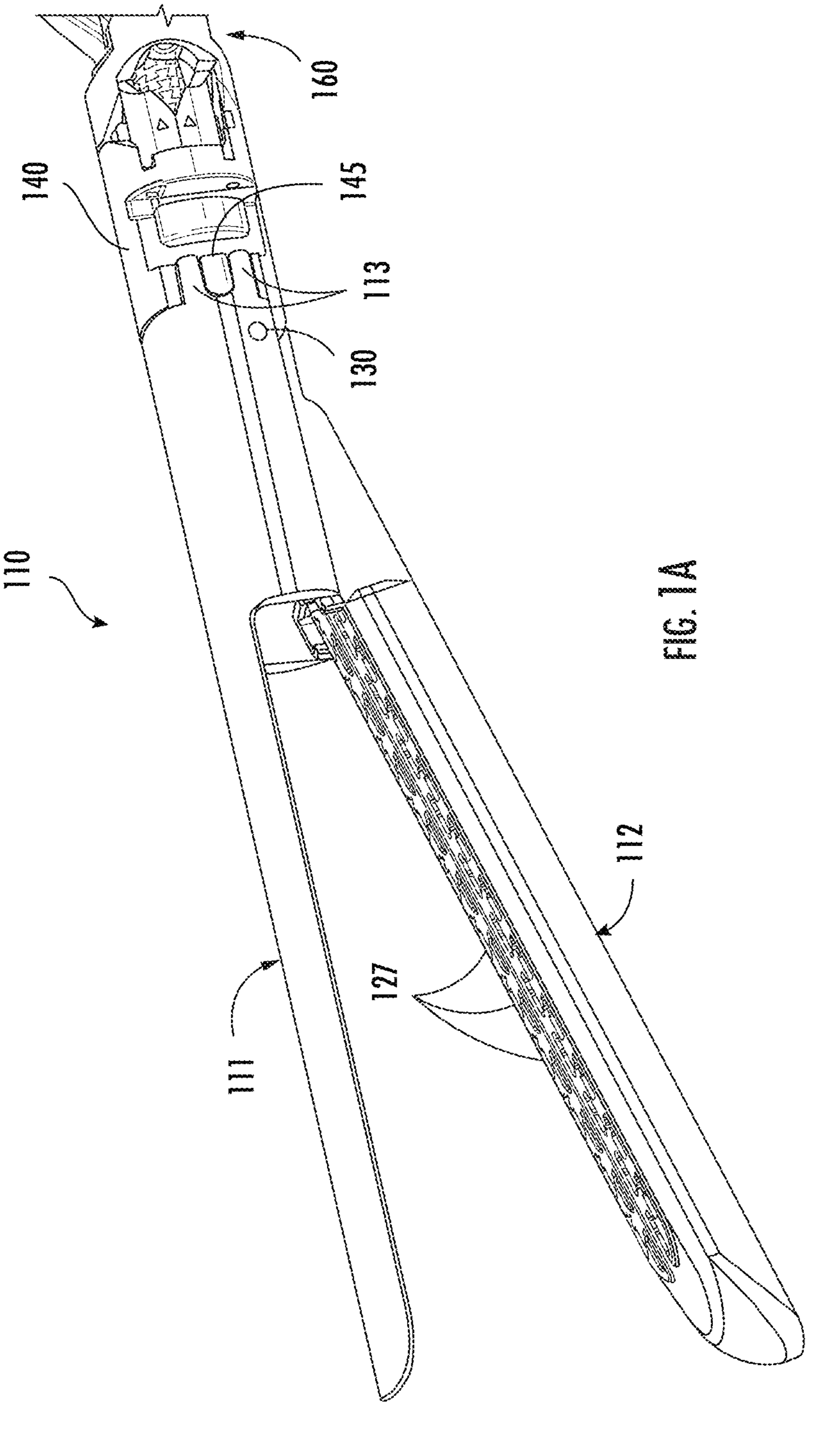
FIG. 1A is a perspective top view of the distal end portion of an illustrative surgical instrument with the jaws in the open position.

FIG. 1A illustrates the distal end portion of surgical instrument 100, including an end effector 110 having first and second jaws 111, 112, a clevis 140 for mounting jaws 111, 112 to the instrument, and an articulation mechanism, such as a wrist 160. First jaw 111 includes an anvil 115 having staple-forming pockets 116 (see FIG. 1D). In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other. In the open position, a fresh stapling cartridge 122 (sometimes referred to as a reload and shown more clearly in FIG. 1B) can be loaded into movable jaw 112 and tissue may be positioned between the jaws 111, 112. In the closed position, jaws 111, 112 cooperate to clamp tissue such that cartridge 122 and anvil 115 are in close cooperative alignment. Movable jaw 112 is configured to move from an open position to a closed position relative to stationary jaw 111.

Figure 1B:
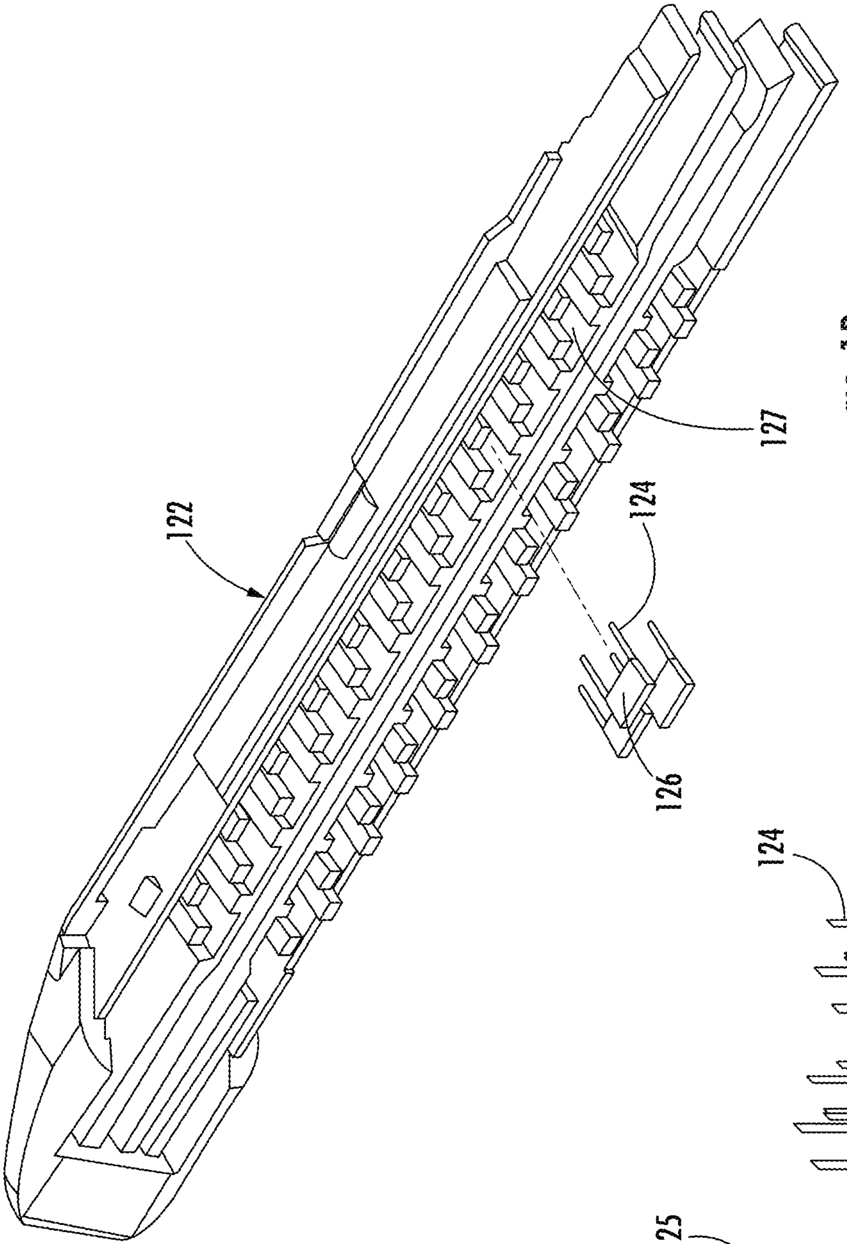
FIG. 1B is a bottom perspective view with parts separated of a representative staple cartridge for an illustrative surgical instrument.
Figure 1C:
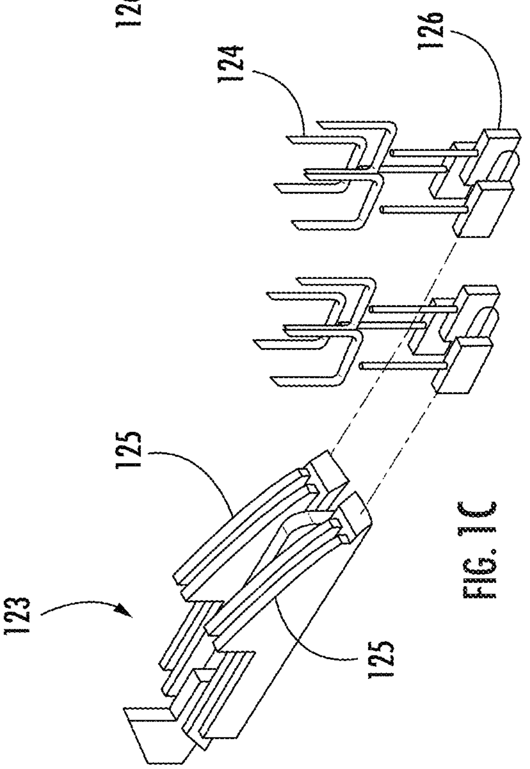
FIG. 1C shows an enlarged view of the cooperative relationship between a portion of a drive member and a plurality of staple pushers and staples which form part of the staple cartridge of FIG. 1B.

Referring now to FIGS. 1B and 1C, a representative staple cartridge 122 may include a plurality of staple assemblies, each comprising one or more staples 124 supported on corresponding staple drivers or pushers 126 provided within respective staple apertures 127 formed in cartridge 122. In certain embodiments, the staple assemblies each include at least one (preferably 2-4) staple pushers 126 removably coupled to at least one (preferably 2-4) staples 124. The staple assemblies are preferably arranged within apertures 127 such that staple pusher 126 is situated near a bottom surface of staple cartridge 122 and staples 124 have their legs facing a top surface of cartridge 122. For ease of reference, the top surface of cartridge 122 faces fixed jaw 111 (see FIG. 1). As discussed above, the entire staple cartridge 122 can be loaded into movable jaw 112 for use in surgery as described in more detail below. In certain embodiments, staple pusher(s) 126 include one or more supporting elements extending above their top surface for providing support to staples 124 when they are resting thereon. Of course, other suitable geometric designs of staple pusher 126 may be used to receive and hold staple 124 in accordance with the present invention. For example, pusher 126 may have a recess (not shown) for receiving staple 124, as is described in commonly-assigned, co-pending International Patent Application No. PCT/US2020/033481, previously incorporated herein by reference. Alternatively, pusher 126 may have a flatter upper surface (i.e., without a recess or pocket) that allows the backspan of staple 124 to rest thereon.

Figure 1D:
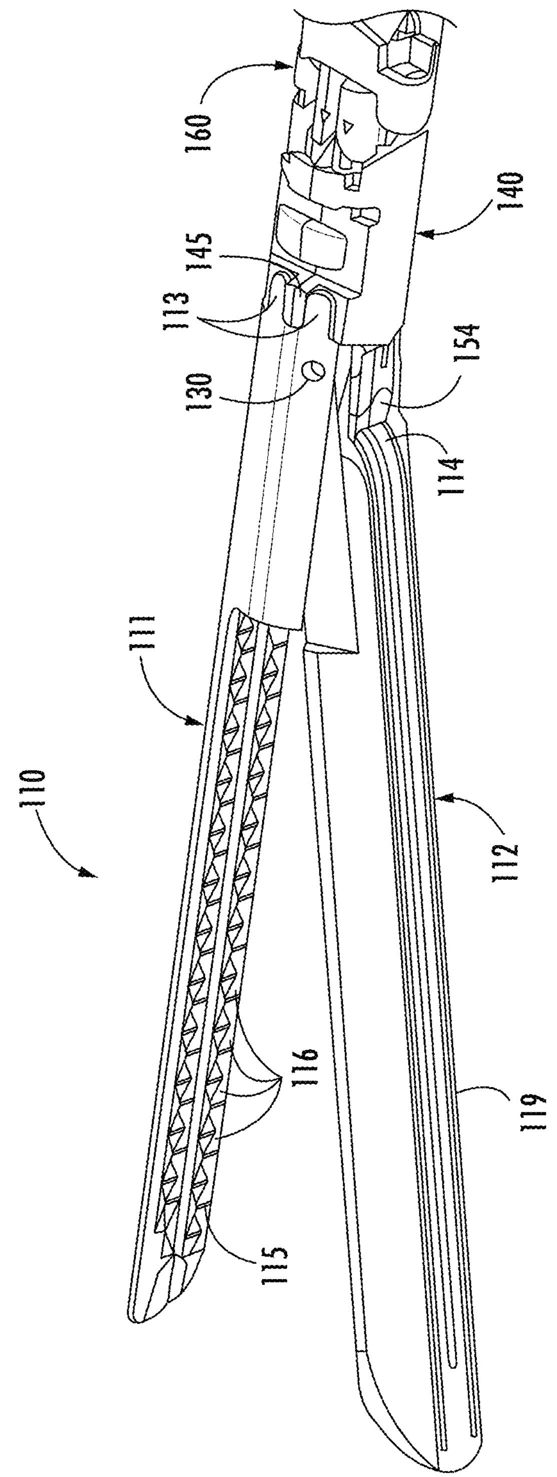
FIG. 1D is a perspective bottom view of the distal end portion of the surgical instrument of FIG. 1A.

Cartridge 122 also may include a shuttle 123 having an inclined distal surface 125 that, upon distal movement, sequentially acts on staple pushers 126, camming them upwardly, thereby moving staples 124 into deforming contact with anvil 115 (See FIG. 1D). Shuttle 123 may be part of a drive member 150 (FIGS. 3A and 3B) described in more detail below. In certain embodiments, drive member 150 may also include a knife 128 configured to translate distally through a channel 119 in cartridge 122 and to sever clamped, stapled tissue (see FIG. 3A). In embodiments, knife 128 may simply be a sharpened edge on drive member 150 rather than a distinct structure within the cartridge. Cartridge 122 may be removably received within movable jaw 112 or, in single use embodiments, may be manufactured as part of movable jaw 112.

In certain embodiments, jaws 111, 112 are attached to surgical instrument 100 via clevis 140. Clevis 140 includes upper and lower portions that cooperate when assembled to form a protrusion 145 configured to engage tabs 113 (see FIG. 1A) of jaw 111 to securely mount jaw 111 in a fixed position on instrument 100. Clevis further includes an opening for receiving a pivot pin 130 defining a pivot axis around which jaw 112 pivots as described in more detail below. A more complete description of a suitable clevis 140 for use with the present invention may be found in commonly-assigned, co-pending provisional patent application No. 62/783,444, filed Dec. 21, 2018; U.S. Pat. No. 62,783,481, filed Dec. 21, 2018; U.S. Pat. No. 62,783,460, filed Dec. 21, 2018; U.S. Pat. No. 62,747,912, filed Oct. 19, 2018; and U.S. Pat. No. 62,783,429, filed Dec. 21, 2018, the complete disclosures of which are hereby incorporated by reference in their entirety for all purposes. Of course, it will be recognized by those skilled in the art that other coupling mechanisms known by those skilled in the art may be used with the present invention to attach the jaws 11, 112 to the proximal portion of surgical instrument 100.

Figure 2:
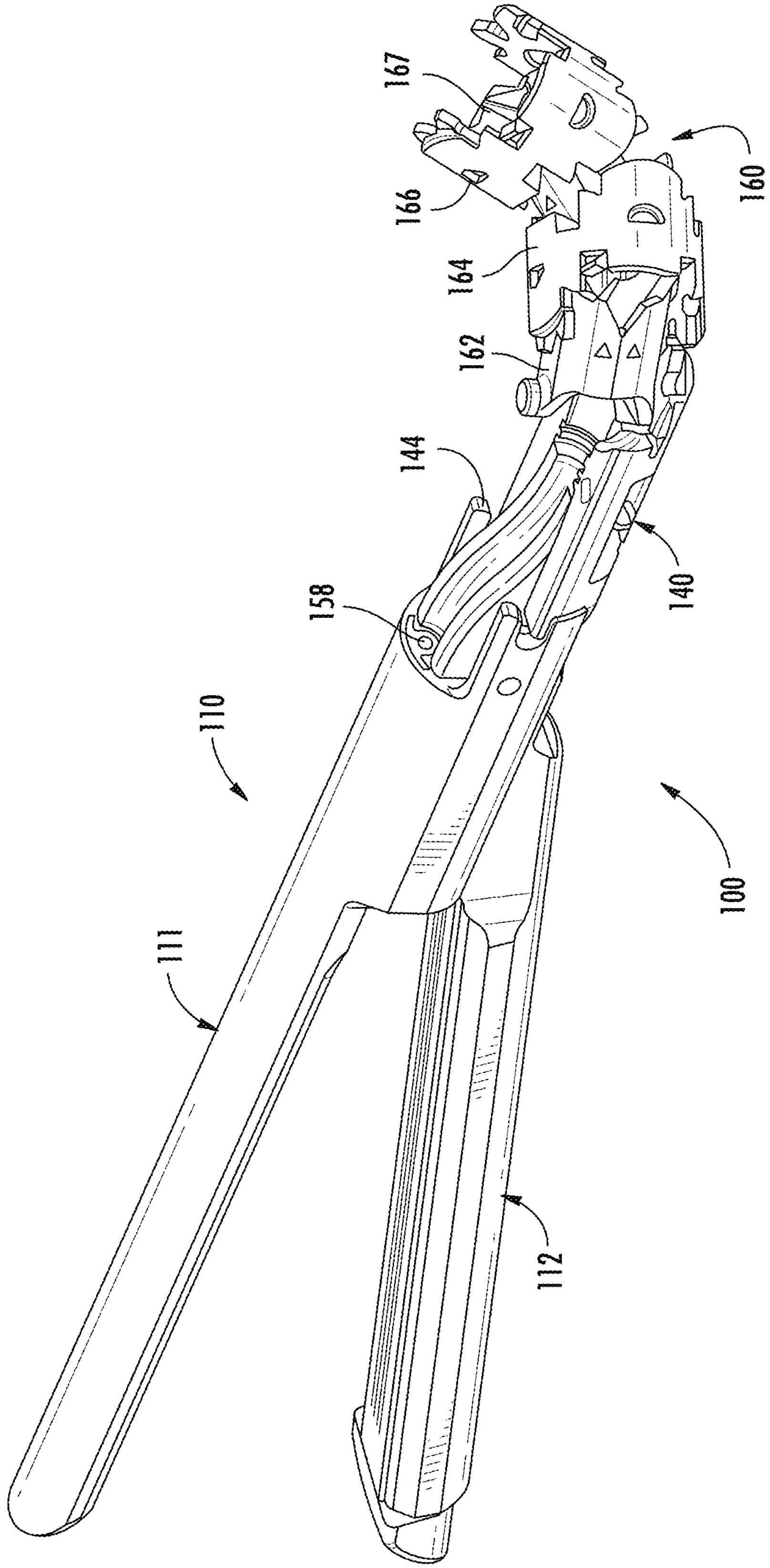
FIG. 2 is a perspective view of the end portion of an illustrative surgical instrument with some parts removed.

Referring now to FIG. 2, end effector 110 may be articulated in multiple directions by an articulation mechanism. In certain embodiments, the articulation mechanism may be a wrist 160 as shown, although other articulation mechanisms are contemplated. A preferred embodiment of wrist 160 includes a plurality of articulation joints 162, 164, 166, etc. that define a bore 167 through which an actuation mechanism (in embodiments, coil 120 and drive cable 171, see FIGS. 3A and 3B) may pass. Upon exiting articulation wrist 160, coil 120 enters and passes through a channel 144 within clevis 140, ultimately engaging bore 158 of upper shoe 152 of drive member 150 (discussed in more detail below). Other articulation mechanisms known by those skilled in the art may substitute for wrist 160 as shown for example in U.S. Publication. No. 2015/0250530 the entire disclosure of which is hereby incorporated by reference in its entirety for all purposes.

Upon actuation of the surgical instrument, drive member 150 is advanced distally through end effector 110 to move jaws 111, 112 from the open position to the closed position, after which shuttle 123 and knife 128 are advanced distally through cartridge 122 to staple and cut tissue grasped between jaws 111, 112. Drive member 150 may be any structure capable of pushing at least one of a shuttle or a knife of a surgical stapling instrument with the necessary force to effectively sever or staple human tissue. Drive member 150 may be an I-beam, an E-beam, or any other type of drive member capable of performing similar functions. Drive member 150 is movably supported on the surgical stapling instrument 100 such that it may pass distally through cartridge 122 and upper fixed jaw 111 and lower jaw 112 when the surgical stapling instrument is fired (e.g., actuated).

Figure 3B:
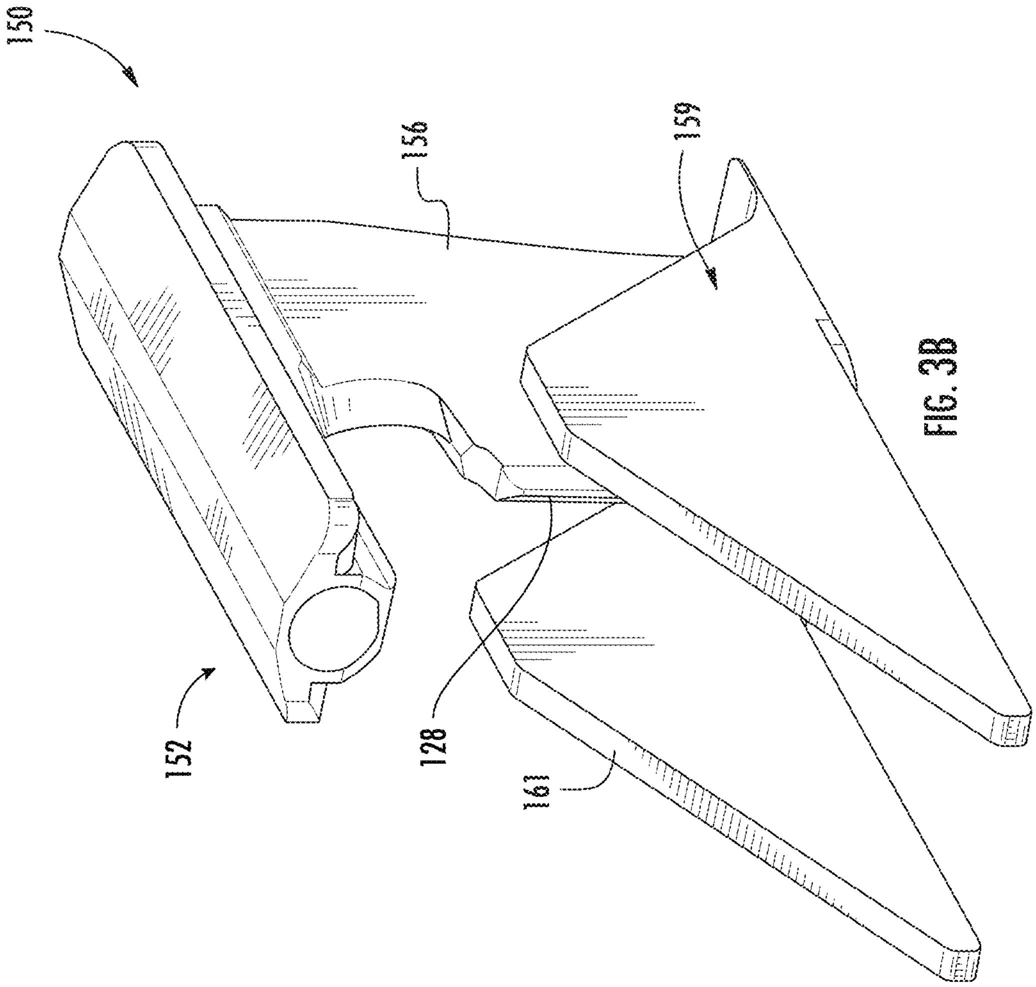
FIG. 3B is a side view of the drive member of FIG. 3A.
Figure 3A:
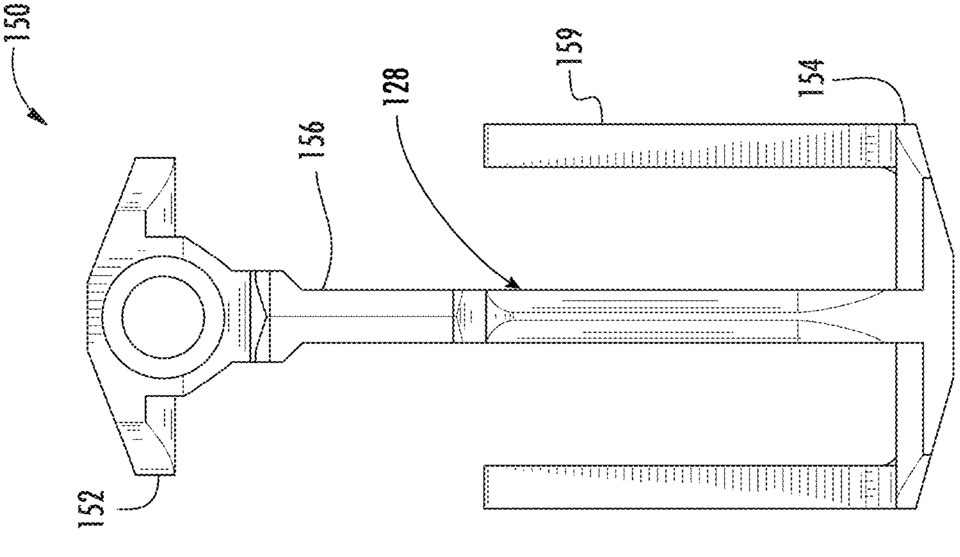
FIG. 3A is a front view of a drive member for the illustrative surgical instrument of FIG. 1.

As seen in FIGS. 3A and 3B, an illustrative drive member 150 may include a body having an upper projection or shoe 152, a lower projection or shoe 154, a central portion 156 and first and second lateral portions 159. Lateral portions 159 are the fins that form shuttle 123 shown earlier. Lateral portions 159 of drive member 150 each comprise distal inclined surfaces or ramps 161 that engage with pushers 126 to drive pushers 126 (and the associated staples 124) vertically or perpendicular to the longitudinal axis of shaft 106 when drive member 150 is translated distally. In a preferred embodiment, shuttle fins 159 are integrated into lower shoe 154 of drive member 150. Integrating shuttle fins 159 into drive member 150 provides more flexibility in the design of staple cartridge 122. For example, this may allow for a reduction in the size of staple cartridge 122 and surgical instrument 100 and/or increasing the length of staples 124 for a given size of surgical instrument 100.

Figure 4A:
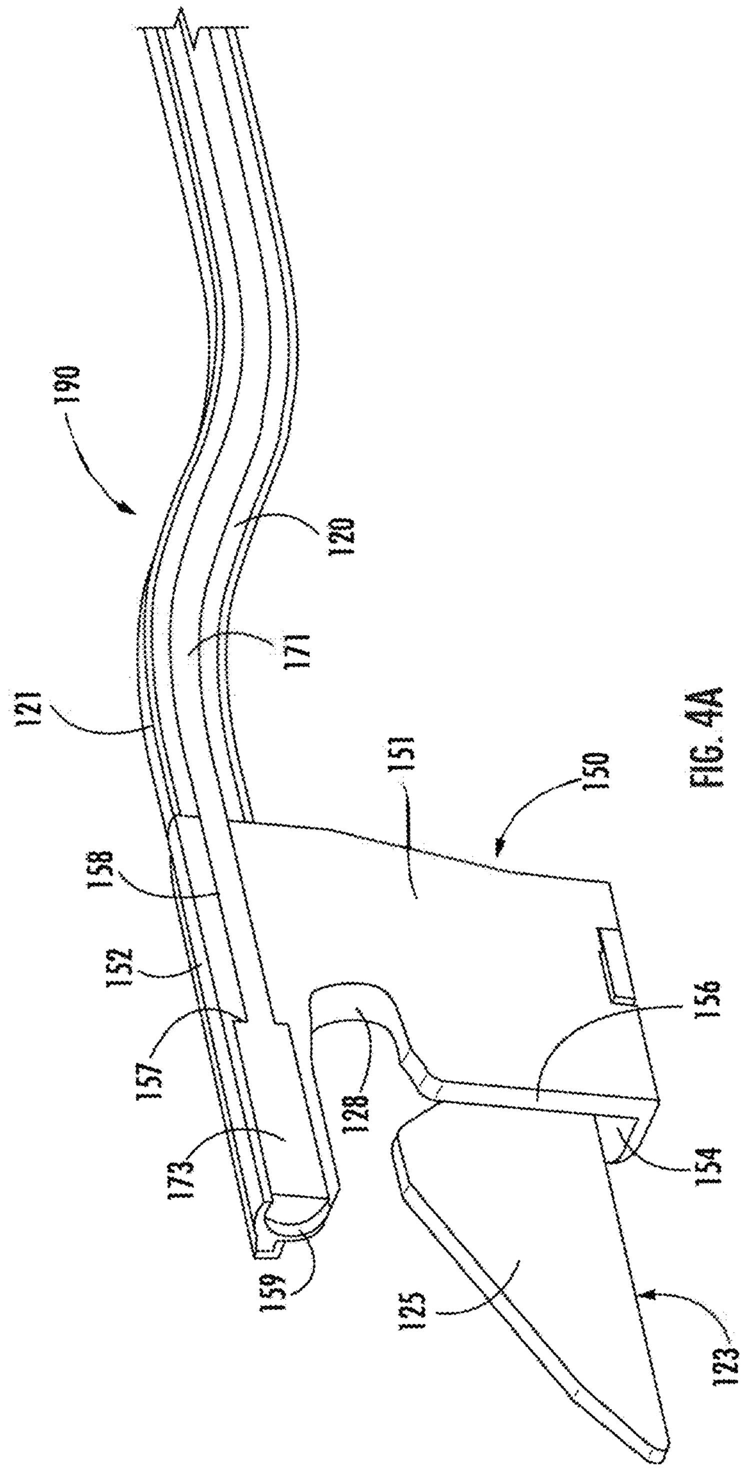
FIG. 4A is a partial cross-sectional view of the actuation mechanism for a drive member for use with the surgical instrument of FIG. 1.
Figure 4B:
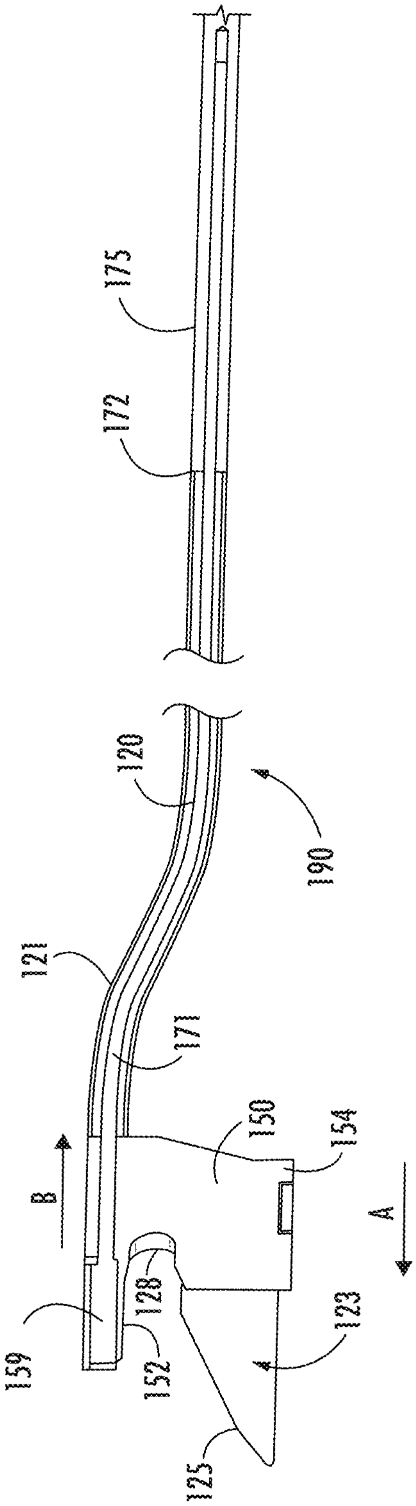
FIG. 4B is a partial cross-sectional view of the actuation mechanism for a drive member for use with the surgical instrument of FIG. 1.

Referring now to FIGS. 4A and 4B, actuation assembly 190 includes a drive cable 171, a coil 120, a sheath 121 surrounding coil 120, and a drive rod 175. Drive cable 171 includes an enlarged distal end 173. Upper shoe 152 of drive member 150 includes a bore 158 into which drive cables 171 are routed. When assembling illustrative surgical instrument 100, coil 120 and a protective sheath 121 are slipped over the free end of drive cable 171. The free end of drive cable 171 is attached to a drive rod 175 securing coil 120 and the protective sheath 121 between drive member 150 and drive rod 175 as best seen in FIG. 3B). Sheath 121 may function to promote stability, smooth movement, and prevent buckling upon actuation of surgical instrument 100. Sheath 121 may be made from polyimide, or any other suitable material having the requisite strength requirements such as various reinforced plastics, a nickel titanium alloy such as NITINOL™, poly para-phenyleneterphtalamide materials such as KEVLAR™ commercially available from DuPont. Those of skill in the art may envision other suitable materials.

Enlarged distal end 173 of drive cable 171 resides within an enlarged distal portion 159 of bore 158 in upper shoe 152 of body 150, such that the proximal face 157 of enlarged distal end 173 may apply a retraction force on upper shoe 152 when the drive cable 171 is pulled proximally, i.e., in the direction of arrow "B" in FIG. 3B. Proximal surface 153 of upper shoe 152 is configured to be engaged by a coil 120 of actuation assembly 190 such that coil 120 may apply force to upper shoe 152 to advance drive member 150 distally, i.e., in the direction of arrow "A" in FIG. 3B. Drive rod 175 is operationally connected to an actuator (e.g., movable handle 102*b*), which allows distal translation and proximal retraction of actuation assembly 190. Those skilled in the art will recognize that in a manually actuated instrument, the actuator may be a movable handle, such as moveable handle 102*b* shown in FIG. 1; in a powered instrument the actuator may be a button (not shown) that causes a motor to act on the drive rod; and in a robotic system, the actuator may be a control device such as the control devices described below in connection with FIGS. 14 and 15. Any suitable backend actuation mechanism for driving the components of the surgical stapling instrument may be used. For additional details relating to exemplary actuation mechanisms using push/pull drive cables see, e.g., commonly assigned, co-pending International Application No. WO 2018/049217, the disclosure of which is hereby incorporated by reference in its entirety for all purposes.

Figure 5:
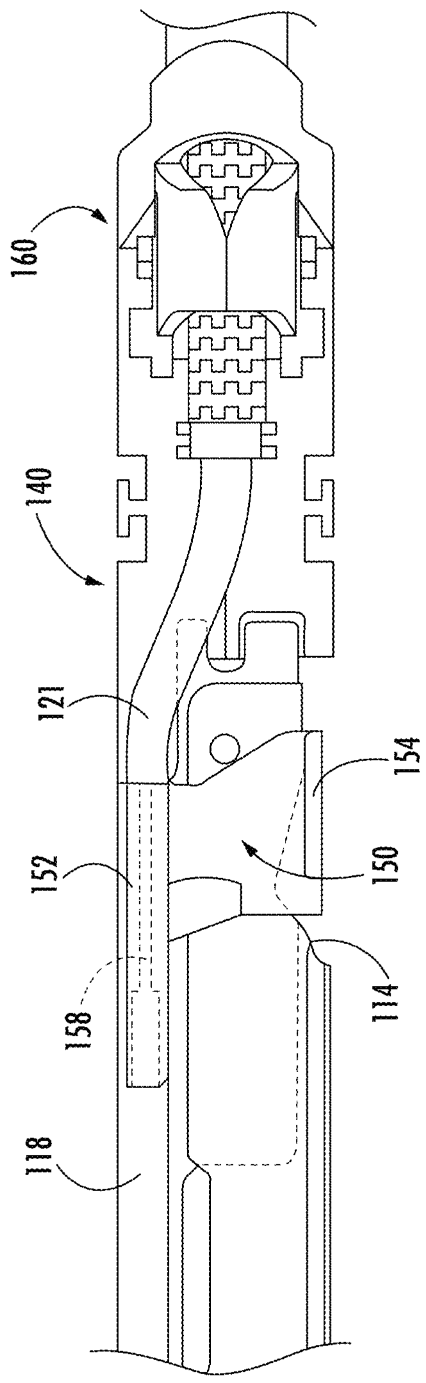
FIG. 5 is a side view of an actuator mechanism for the illustrative surgical instrument of FIG. 1.

Referring now to FIG. 5, upper shoe 152 of drive member 150 is substantially aligned with and translates through a channel 118 in fixed jaw 111, while lower shoe 154 of drive member 150 is substantially aligned with and translates through a channel (not shown) in jaw 112 and below jaw 112. During actuation of illustrative surgical instrument 100, drive rod 175 applies force to coil 120, thereby causing coil 120 to apply force to upper shoe 152 of drive member 150, translating it distally (i.e., in the direction of arrow "A" in FIG. 3B) initially closing jaws 111,112 and then ejecting staples 124 from cartridge 122 to staple tissue. After stapling is complete, drive rod 175 applies a force in the proximal direction to effect retraction of drive member. During retraction, enlarged distal end 173 of drive cable 171 is obstructed by wall 157 of enlarged portion 159 of bore 158, causing drive cable 171 to apply force to upper shoe 152 of drive member 150, thereby translating drive member 150 in the proximal direction. One of ordinary skill in the art will appreciate that drive member 150, drive cable 171, and drive rod 175 all move in unison and remain in the same relative position to each other.

In use, in the open configuration, drive member 150 is positioned proximally of cam surface 114 formed on movable jaw 112. As drive member 150 translates in the distal direction, movable jaw 112 will rotate towards the closed position around pivot 117. Once drive member 150 has come into contact with cam surface 114 of movable jaw 112, lower portion 154 of drive member 150 rides underneath cam surface 114, drive member 150 pushes movable jaw 112, causing it to pivot towards the closed position. In the closed position, drive member 150 has translated distally past cam surface 114. In this position, tissue is clamped, and further advancement of the drive member will sever and staple tissue. Of course, it will be recognized by those skilled in the art that drive member 150 may be any structure capable of pushing at least one of a shuttle or a knife of a surgical stapling instrument with the necessary force to effectively sever or staple human tissue. Drive member 150 may be an I-beam, an E-beam, or any other type of drive member capable of performing similar functions. Drive member 150 is movably supported on the surgical stapling instrument 100 such that it may pass distally through a staple cartridge and upper fixed jaw 111 and lower jaw 112 when the surgical stapling instrument is fired (e.g., actuated).

Figure 6:
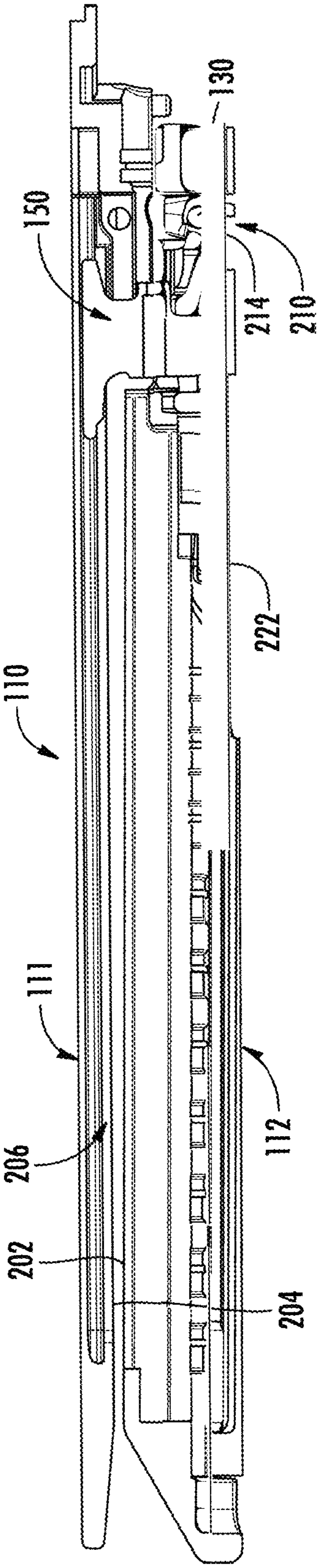
FIG. 6 is a side view of an end effector of a surgical instrument with parts removed according to certain embodiments of the invention.

Referring now to FIG. 6, a preferred embodiment of end effector 110 according to the present disclosure includes fixed jaw 111 and movable jaw 112 as discussed above in relation to the illustrative surgical instrument 100. Movable jaw 112 includes a staple cartridge 122 for housing staples 126, as discussed above and shown in FIG. 1B. Jaw 112 preferably has an upper surface 202 opposite a lower surface 204 of fixed jaw 111. In the closed position of jaws 111, 112, upper and lower surfaces 202, 204 define a gap 206 therebetween that provides clearance space for tissue after the tissue has been clamped by jaws 111, 112. In the exemplary embodiment, upper surface 202 is substantially parallel to lower surface 204 in the closed position such that gap 206 has a fixed dimension along the longitudinal axis of end effector 110 (note that the closed position is not shown in FIG. 6). The thickness of this tissue gap 206 will depend on the clinical application, e.g., the amount of tissue to be clamped, the height of staples 124, etc.

Fixed and movable jaws 111, 112 include first and second longitudinal slots, respectively, (not shown) each configured to receive a lateral projection from drive member 150. In the preferred embodiment, the length of the first longitudinal slot (i.e., in the fixed jaw 111) is greater than the length of the second longitudinal slot in the movable jaw 112. In certain embodiments, the first longitudinal slot extends from the proximal end of fixed jaw 111 to the distal end of fixed jaw 111, and the second longitudinal slot extends from about a midway position between the proximal end of movable jaw 112 and the distal end of the second jaw, to the distal end of movable jaw 112. In the overclosed position, drive member 150 is in a retracted position in which the second lateral projection of drive member 150 is not engaged with movable jaw 112 and is not received within the second longitudinal slot of movable jaw 112.

Movable jaw 112 is pivotally coupled to fixed jaw 111 by a hinge 210 positioned at the proximal end portion of end effector 110. Hinge 210 preferably comprises a pin 130 or other suitable projection that extends through a hole (not shown) in a joint structure 214 coupled to the proximal portion of movable jaw 112. Pin 130 acts as a pivot to allow movable jaw 112 to pivot relative to fixed jaw 111 about the axis extending through pin 130. Of course, other suitable hinges may be used with the present disclosure, such as a bolt, joint hinge, strap hinge, butterfly, barrel, piano, pivot, spring, "living hinges" and the like. In the exemplary embodiment, hinge 210 allows movable jaw 112 to pivot from an open position, wherein movable jaw 112 extends downward from fixed jaw 111 such that an area larger than tissue gap 206 exists between jaws 111, 112 (see, for example, FIG. 1A), to a closed position, wherein upper and lower surfaces 202, 204 of jaws 111, 112 are substantially parallel to each other, as discussed above. In addition, and according to the present disclosure, hinge 200 allows movable jaw 112 to pivot upwards from the closed position towards fixed jaw 111 into an "overclosed" position (shown in FIG. 6) wherein at least a portion of tissue gap 206 has a smaller thickness than in the closed position.

Figure 8:
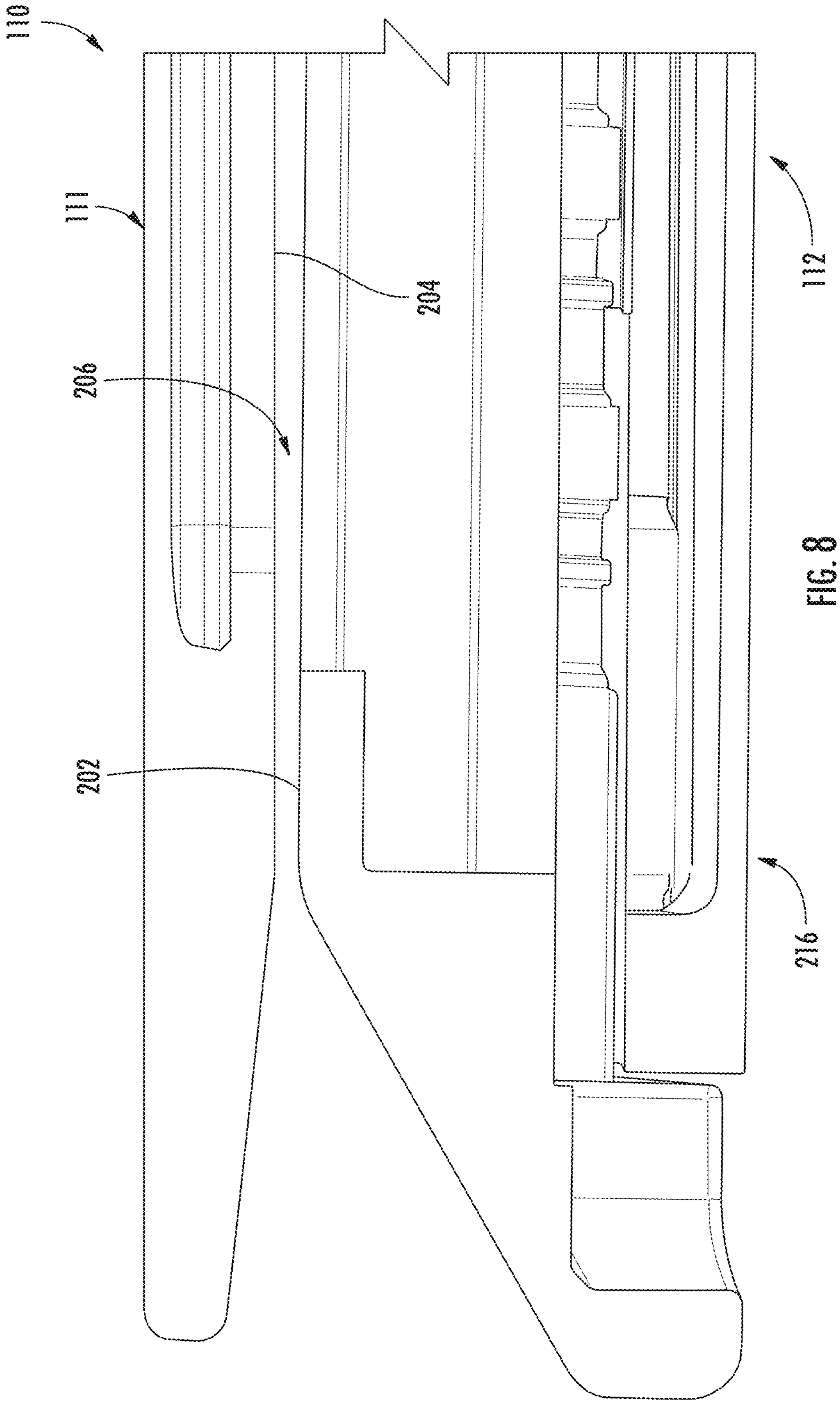
FIG. 8 is a side view of a distal portion of the end effector of FIG. 6.

In particular and as shown in FIG. 8, a distal end portion 216 of movable jaw 112 is closer to fixed jaw 111 in the overclosed position such that tissue gap 206 is no longer parallel. Thus, upper surface 202 of movable jaw 112 extends at an angle relative to the longitudinal axis of end effector 110 in the overclosed position. In the exemplary embodiment, this angle is between about 0.4 to about 2.0 degrees, preferably between about 0.5 to about 1.0 degrees and more preferably about 0.55 degrees relative to the longitudinal axis of end effector 110.

In the overclosed position, the distance separating an outer surface of the distal end of fixed jaw 111 from an outer surface of the distal end of movable jaw 112 is approximately equal to a distance separating an outer surface of the proximal end of fixed jaw 111 from an outer surface of the proximal end of movable jaw 112. In the closed position, the distance separating an outer surface of the distal end of fixed jaw 111 from an outer surface of the distal end of movable jaw 112 is greater than the distance separating an outer surface of the proximal end of fixed jaw 111 from an outer surface of the proximal end of movable jaw 112. Thus, the total cross sectional area of the distal end of end effector 110 is approximately equal to the total cross sectional area of the proximal end of end effector 110 in the overclosed position. However, the total cross sectional area of the distal end of end effector 110 is larger than the total cross sectional area of proximal end of end effector in the closed position.

In the overclosed position, the tissue contact surface of movable jaw 112 and the second longitudinal slot in movable jaw 112 are not parallel (i.e., transverse) to the longitudinal axis of fixed jaw 111. In the closed position, the tissue contact surface of movable jaw 112 and the second longitudinal slot in movable jaw 112 are substantially parallel to the longitudinal axis of fixed jaw 111

Figure 7:
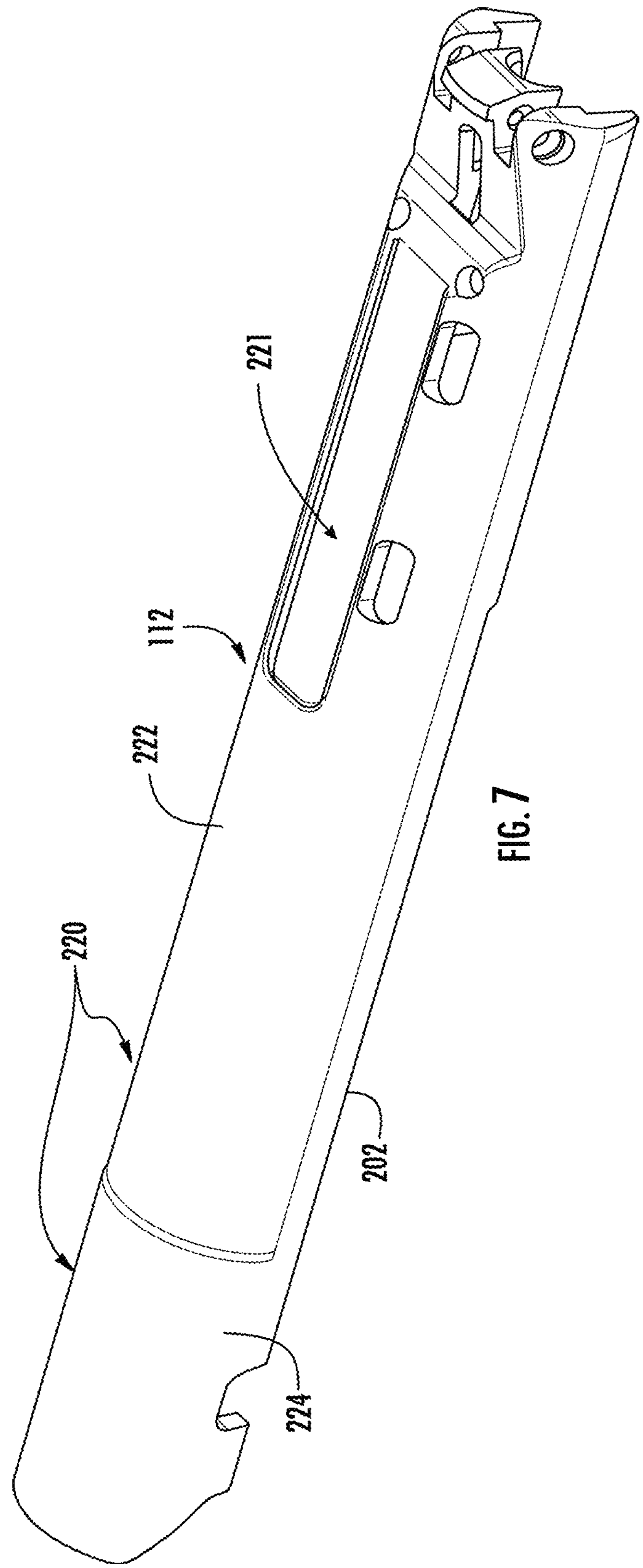
FIG. 7 is a perspective bottom view of one portion of a movable jaw of an end effector according to certain embodiments of the present invention.

Referring now to FIG. 7, movable jaw 112 preferably comprises a curved lower surface 220 that extends below jaw 112 from one side of upper surface 202 to the other side of upper surface 202. In certain embodiments, lower surface 220 further includes a proximal portion 222 that is recessed from the rest of lower surface 220. Essentially, a small amount of material is cut away from lower surface 220 at proximal portion 222 after the part has been molded such that proximal portion 222 has a smaller radius than a distal portion 224 of jaw 112 in the closed position. The depth and overall size of the recess in proximal portion 222 is preferably designed to provide sufficient room for tissue gap 206 to be taken up distally, while maintaining suitable stiffness for jaw 112 in operation. In addition, the recess in proximal portion 222 is preferably sized to limit any sharp edges created wherein the recess intersects the track or channel 119 in jaw 112. Removing this material from proximal portion 222 of lower surface 220 reduces the overall cross-sectional size of end effector 110 such that lower surface 220 of jaw 112 is substantially coradial with the upper surface of fixed jaw 111 in the overclosed position. (i.e., proximal portion 222 does not "stick out" below end effector 110 when distal portion 224 is pivoted upwards into the overclosed position). This allows the entire end effector 110 to fit within a cannula having a smaller radius when jaws 111, 112 are placed into the overclosed position.

Alternatively, the entire lower surface 220 of jaw 112 may be designed with an incline that substantially matches the angle that jaw 112 makes with the longitudinal axis of end effector 110 in the overclosed position (i.e., about 0.4 to about 2.0 degrees, preferably about 0.5 to about 1.0 degrees and more preferably about 0.55 degrees relative to the longitudinal axis). The incline extends in the proximal direction such that distal portion 224 of jaw 112 is further away from jaw 111 than proximal portion 222 in the closed position. In this configuration, lower surface of jaw 112 will be substantially parallel to the longitudinal axis in the overclosed position and end effector 110 will have a small cross-sectional area.

In an exemplary embodiment, hinge 210 is not locked into any one position such that movable jaw 112 may freely pivot from the open position (FIG. 1A), through the closed "parallel" position (not shown), to the overclosed position shown in FIGS. 6 and 8. Hinge 210, however, is configured to limit movable jaw 112 from moving beyond the overclosed or open positions (i.e., the freedom of movement is limited to the angle between the overclosed and open positions). Hinge 210 may be biased towards the open position such that movable jaw 112 will move into this position unless constrained. In certain embodiments, the surgical instrument further comprises a spring (not shown) configured to apply a jaw-opening force to at least one of the fixed and movable jaws 111, 112. Alternatively, movable jaw 112 may be positioned below fixed jaw 111 during operation such that gravity automatically biases movable jaw 112 towards the open position. In the preferred embodiment, drive member 150 is proximal to movable jaw 112 in its insertion or "home" position so that it does not interfere with the pivoting of jaw 112.

In use, the operator (e.g., surgeon) holds jaws 111, 112 together in the overclosed position before inserting end effector 110 into a cannula or other percutaneous penetration in the patient. Once in the cannula, the internal surface of the cannula will hold jaws 111, 112 in the overclosed position, thereby reducing the radius of end effector 110 and allowing end effector 110 to fit through a smaller cannula. After end effector 110 passes through the cannula and into a body cavity of the patient, movable jaw 112 will pivot from the overclosed position through the closed position and into the open position for placing tissue into jaws 111, 112 at the target site within the patient. The surgeon may then place jaws 111, 112 around the target tissue and actuate drive member 150 to move distally and come into contact with cam surface 114 of movable jaw 112. As discussed previously, lower portion 154 of drive member 150 rides underneath cam surface 114 and drive member 150 pushes movable jaw 112, causing it to pivot towards the closed position (see FIG. 5). In the closed position, drive member 150 has translated distally past cam surface 114. In this position, tissue is clamped, and further advancement of the drive member will sever and staple tissue.

Upon completion of the surgical operation, end effector 110 is retracted through the cannula or percutaneous penetration in the patient. The inner surface of the cannula forces movable jaw 112 back into the overclosed position so that the cross-sectional area of end effector 110 is small enough to fit through the cannula. Thus, the tissue gap 206 that is necessary for clamping onto tissue can at least be partially eliminated in the overclosed position so that the end effector 110 can be made smaller for insertion or retraction through the cannula.

In an alternative embodiment, surgical instrument 100 includes a locking mechanism (not shown) for locking hinge 210 into either the closed or the overclosed positions. In the latter instance, the end effector 110 may be freely moved around within the body cavity of the patient in the overclosed position, making it more compact and maneuverable. The locking mechanism may be coupled to a suitable actuator on the proximal handle (or as part of a robotic control system) so that the operator may unlock hinge 210 and allow it to pivot into the open position. Alternatively, drive member 150 may include a camming or other surface that engages the locking mechanism to unlock hinge 210. In this latter embodiment, the camming surface may reside on a distal or proximal end portion of drive member 150 such that distal or proximal movement of drive member 150 engages the locking mechanism to unlock hinge 210 and allow jaw 112 to pivot away from jaw 111 into the open position. The locking mechanism may include a spring-loaded unlocking/locking member (not shown). In this embodiment, distal translation of drive member 150 would allow the locking/unlocking member the freedom to move in the direction of spring force to, for example, unlock hinge 210 and allow jaws 111, 112 to pivot freely. Proximal translation of drive member 150 forces the locking/unlocking mechanism back in the direction opposite the spring force to lock hinge 210 in the overclosed position.

Figure 9:
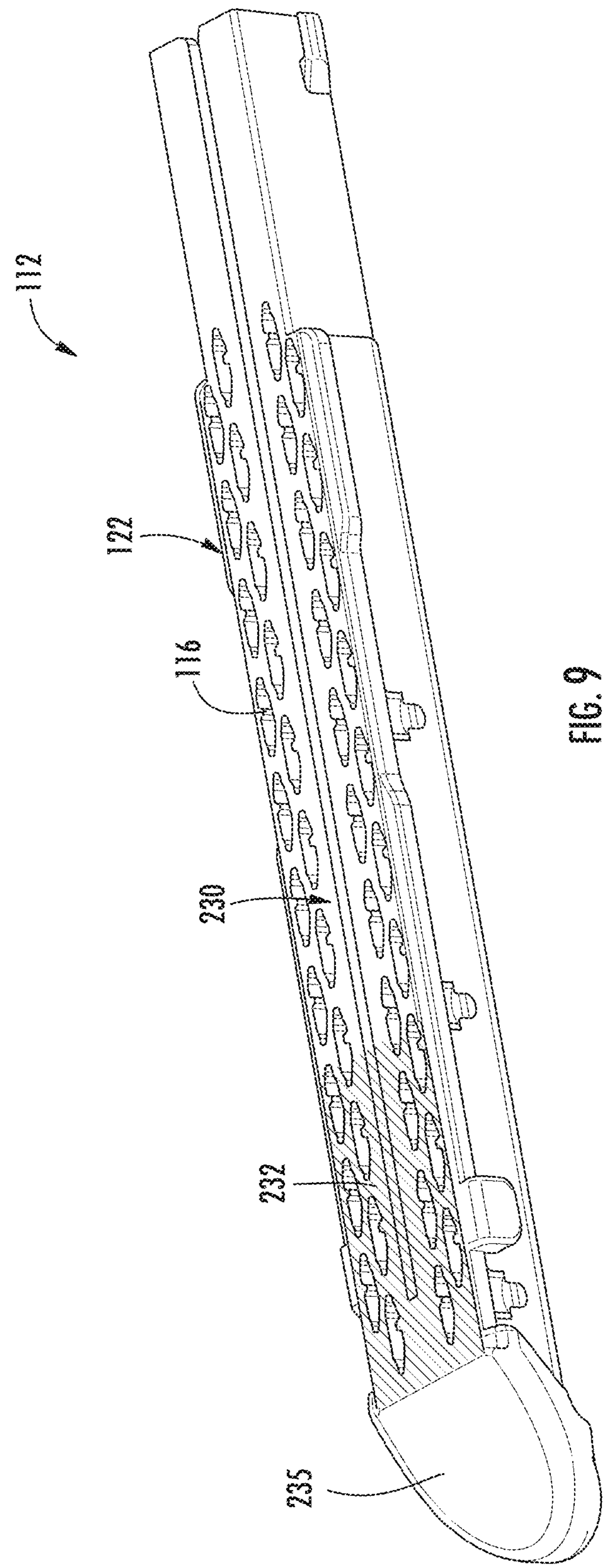
FIG. 9 is a top view of distal portion of a movable jaw of an end effector according to certain embodiments of the present invention.

Referring now to FIG. 9, another embodiment of staple cartridge 122 includes a top surface 230 with pockets 116 for housing staples 124 (not shown). In this embodiment, top surface 230 of cartridge 122 includes a distal end portion 232 that is inclined relative to a proximal portion 234 of surface 230. In particular, distal end portion 232 is inclined downward towards the distal tip 235 of cartridge 122 so as to provide more clearance in tissue gap 206 between jaws 111, 112 in the overclosed position. In the exemplary embodiment, distal end portion 232 is inclined at an angle relative to the longitudinal axis of end effector 110 that substantially matches the angle formed by movable jaw 112 with fixed jaw 111 in the overclosed position. This configuration provides clearance for movable jaw 112 to be moved into the overclosed position without contacting lower surface 204 of fixed jaw 111. Certain staple cartridges 122 are larger than others (e.g., taller staples) and other staple cartridges 122 are designed with camber such that the distal end portion has a tighter tissue gap than the proximal end portion. These latter staple cartridges 122 are typically used on tissue or blood vessels that are not placed at the tip of the device (i.e., vessels that are clamped in the central and/or proximal portion of jaws 111, 112). This embodiment allows use of those types of suture cartridges with the present invention.

FIGS. 10-13 illustrate embodiments of the present disclosure for setting multiple thicknesses for tissue gap 206 between jaws 111, 112. In these embodiments, drive member 150 has first and second lateral projections and fixed jaw 111 defines first and second longitudinal slots each configured to accommodate the first lateral projection of drive member 111. Movable jaw 112 defines a third longitudinal slot configured to accommodate the second lateral projection of drive member 150. During a first operational mode, the first lateral projection travels within the first longitudinal slot of fixed jaw 111. During a second operational mode, the first lateral projection travels within the second longitudinal slot of the fixed jaw 111. The surgical instrument further comprises an actuator configured to switch between the first operational mode and the second operational mode. FIGS. 10-13 illustrate different embodiments of the actuator.

Figure 10A:
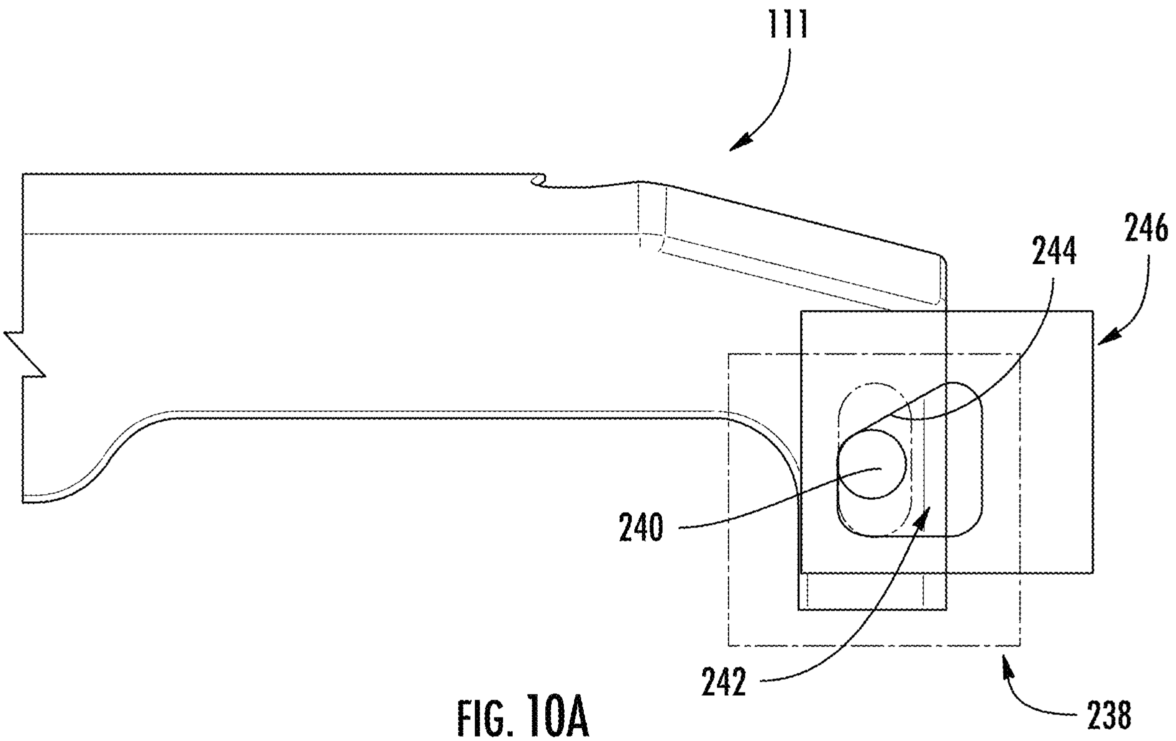
FIGS. 10A and 10B are side views of a proximal portion of a jaw of an end effector according to certain embodiments of the present invention.
Figure 10B:
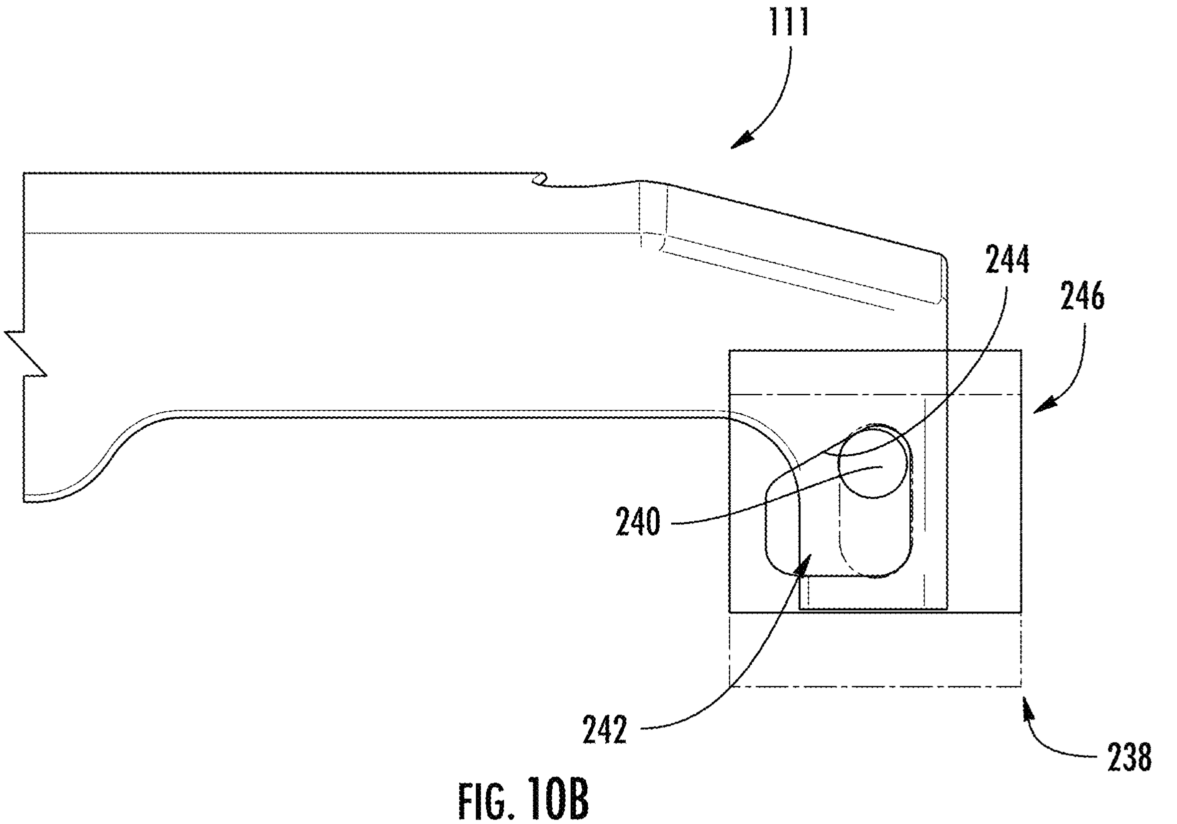

Referring now to FIGS. 10A and 10B, in one embodiment, fixed jaw 111 includes a slide plate 238 and a projection or pin 240 extending laterally outward from the body of jaw 111 through an opening in slide plate 238. Pin 240 is configured to extend through an opening 242 in a second slide plate 246 coupled to drive member 150 such that pin 240 cooperates with a camming surface 244 in plate 246. Alternatively, plate 246 may be coupled to, or integral with jaw 111 with pin 240 extending from drive member 150. As drive member 150 is translated distally, camming surface 244 motivates projection 240 (and jaw 111 therewith) upward relative to movable jaw 112 (not shown in FIGS. 9A and 9B). This increases the thickness of tissue gap 206. Alternatively, projection 240 and slide plate 246 may cooperate with movable jaw 112 such that movable jaw 112 is configured to translate relative to fixed jaw 111. In use, jaws 111, 112 are set in the overclosed position (FIG. 10A) during insertion, removal and maneuvering of the device within the patient. When the operator is prepared to clamp tissue, drive member 150 is moved distally, causing fixed jaw 111 to translate in a direction substantially perpendicular to the longitudinal axis of end effector 110 (i.e., away from movable jaw 112). This increases the size of the entire tissue gap 206 to allow room for clamping tissue. In this embodiment, jaws 111, 112 may remain substantially parallel to each other in both the closed and overclosed positions.

Figure 11:
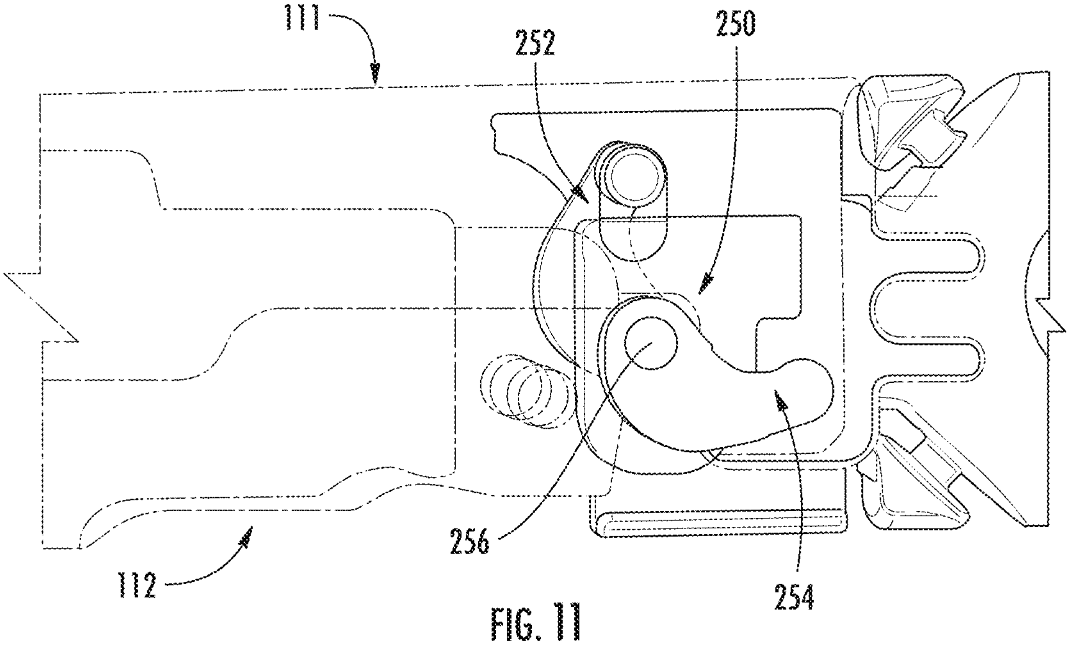
FIG. 11 is a partially transparent side view of a proximal portion of an end effector according to certain embodiments of the present invention.

Referring now to FIG. 11, another embodiment of the present invention includes a linkage 250 coupling fixed jaw 111 with drive member 150 (not shown in FIG. 11). As shown, linkage 250 includes first and second coupling elements 252, 254 pivotally coupled together with a hinge pin 256. First coupling element 252 is coupled to drive member 150 and second coupling element 254 is coupled to jaw 111. In use, drive member 150 is translated longitudinally, causing coupling elements 252, 254 to pivot about hinge 256 and translate jaw 111 in a transverse direction to the longitudinal axis, thereby moving jaw 111 towards and away from movable jaw 112 and changing the thickness of tissue gap 206. As in the previous embodiment, linkage 250 may couple drive member 150 to movable jaw 112 in a similar manner. Alternatively, linkage 250 may be coupled to a proximal actuator (not shown) that moves one or both jaws 111, 112 independently of drive member 150. In this embodiment, the operator, for example, may engage the actuator from handle 102, or from another user interface such as a robotic control device, to move jaws 111, 112 between the closed and overclosed positions.

Figure 12:
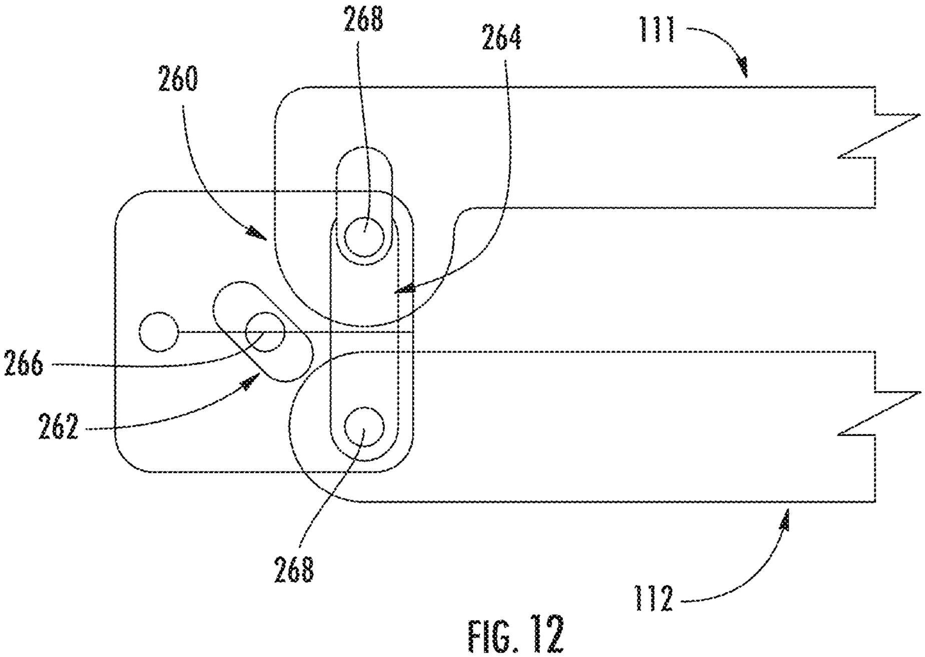
FIG. 12 is a side view of an actuation mechanism for moving jaws of an end effector according to certain embodiments of the present disclosure.

FIG. 12 illustrates yet another embodiment of the present invention. As shown, end effector 110 includes a rotatable drive assembly 260 comprising a drive member 262 rotatably coupled to a proximal end portion of end effector 110 by a pin 266 or other suitable hinge. A linkage 264 is pivotally coupled to fixed jaw 111 and movable jaw 112. Drive member 262 is configured to rotate about pin 266 and engage linkage 264, causing linkage 264 to pivot about pins 268 or other suitable hinges in jaws 111, 112. Linkage 264 pivots and causes fixed jaw 111 to translate distally and downwards relative to movable jaw 112 into the overclosed position, thereby reducing the tissue gap 206 therebetween. Alternatively, linkage 264 may be designed to translate movable jaw 112 relative to fixed jaw 111. In yet another alternative, drive member 262 may be coupled to drive member 150 and configured to rotate upon distal or proximal translation of drive member 150. End effector 110 may further include a locking mechanism to hold drive member 262 in position (either in the closed or overclosed position of jaws 111, 112). Note that jaws 111, 112 may remain substantially parallel to each other in both the closed and overclosed positions. This allows the operator to set multiple tissue gap settings for different staple cartridges, as discussed in more detail below.

Figure 13A:
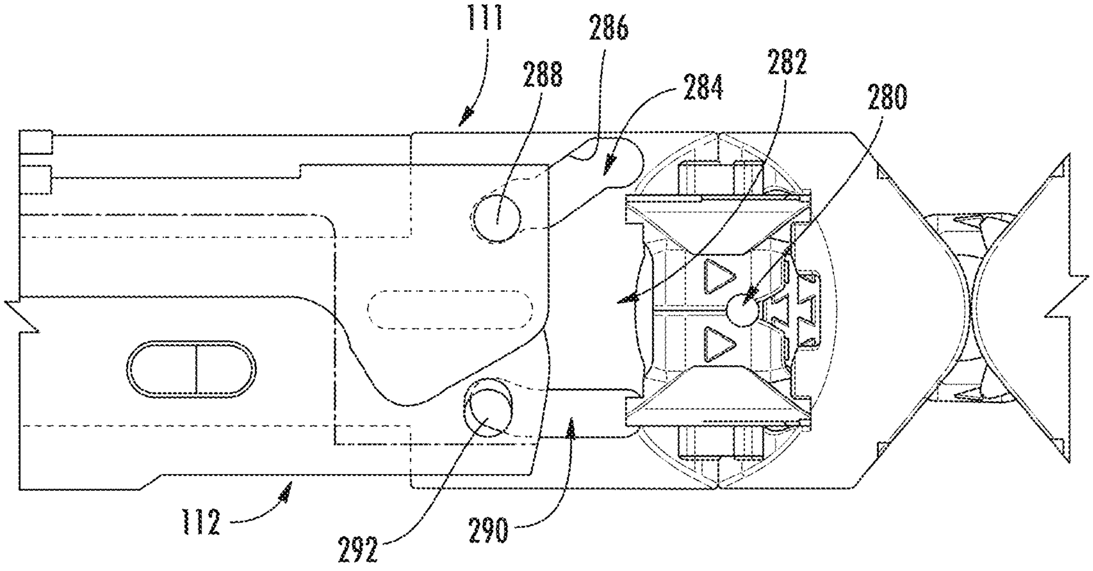
FIGS. 13A and 13B are partially transparent side views of a proximal portion of an end effector according to certain embodiments of the present disclosure.
Figure 13B:
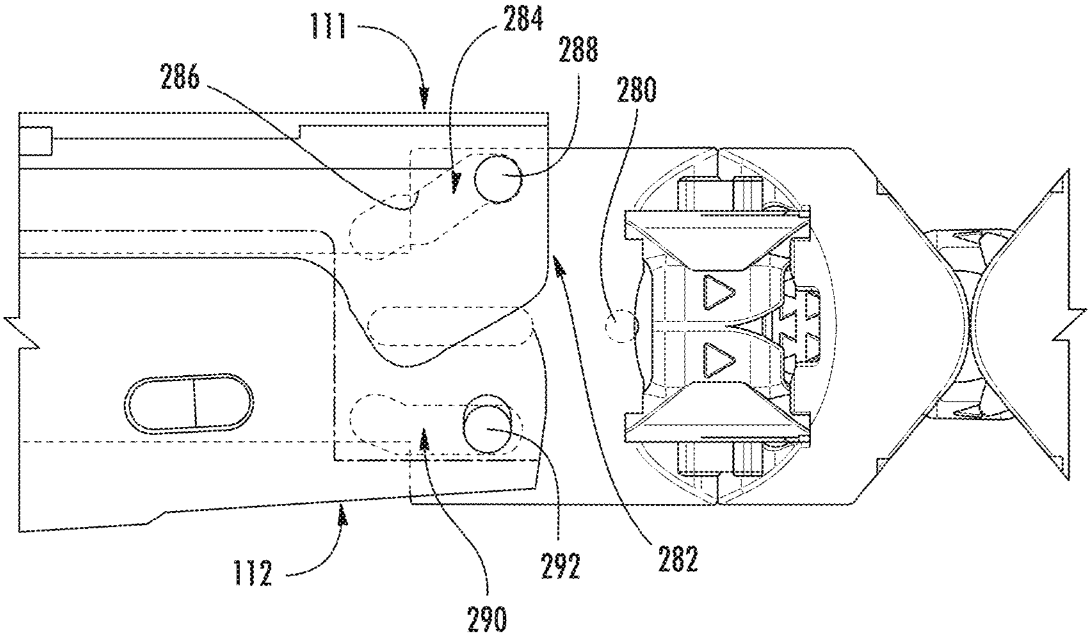

FIGS. 13A and 13B illustrate another embodiment for moving jaws 111, 112 between the closed and overclosed positions. As shown in FIG. 13A, a laser-cut tube 280 is coupled to a cam mover plate 282 having an opening 284 defining an inclined camming surface 286. Fixed jaw 111 includes a projection or pin 288 that extends through opening 284 in plate 282. Tube 280 may be coupled to drive member 150 or a suitable actuator at the proximal end of instrument 100. Translation of drive member 150 and/or actuation by the operator via a user interface causes tube 280 to translate in the distal direction, thereby translating cam mover plate 282. Pin 288 on jaw 111 is cammed upwards to translate jaw 111 away from jaw 112 (see FIG. 13B). This moves jaws 111, 112 from the overclosed position (FIG. 13A) to the closed position (FIG. 13B). Cam mover plate 282 may also include a second opening 290 for receiving a projection or pin 292 on lower movable jaw 112. Second opening 290 may also have a cammed surface such that both jaws 111, 112 are translated vertically upon longitudinal translation of tube 280 and plate 282. Alternatively, cam mover plate 282 may only have cammed surfaces that engage lower movable jaw 112.

Of course, it will be recognized that the present invention is not limited to the embodiments shown above for moving first and second jaws 111, 112 between the closed and overclosed positions. For example, instrument 100 may include an actuator, such as the cable drive actuator described above in reference to drive member 150, that is coupled to a user interface on the proximal handle of instrument 100 or to a robotic control assembly (discussed below). The actuator may be designed to drive a rack-pinion, gear-gear drive, cable or belt drive or other suitable driving mechanism to translate one of the jaws up and down relative to the other one. In this embodiment, the cable drive actuator may be suitably coupled to one or both of jaws 111, 112 to allow the operator to move jaws 111, 112 between the closed and overclosed positions through the proximal interface. A locking/unlocking mechanism may be coupled to either the cable drive or the driving mechanism to hold the mechanism in place at a selected jaw position.

Figure 14:
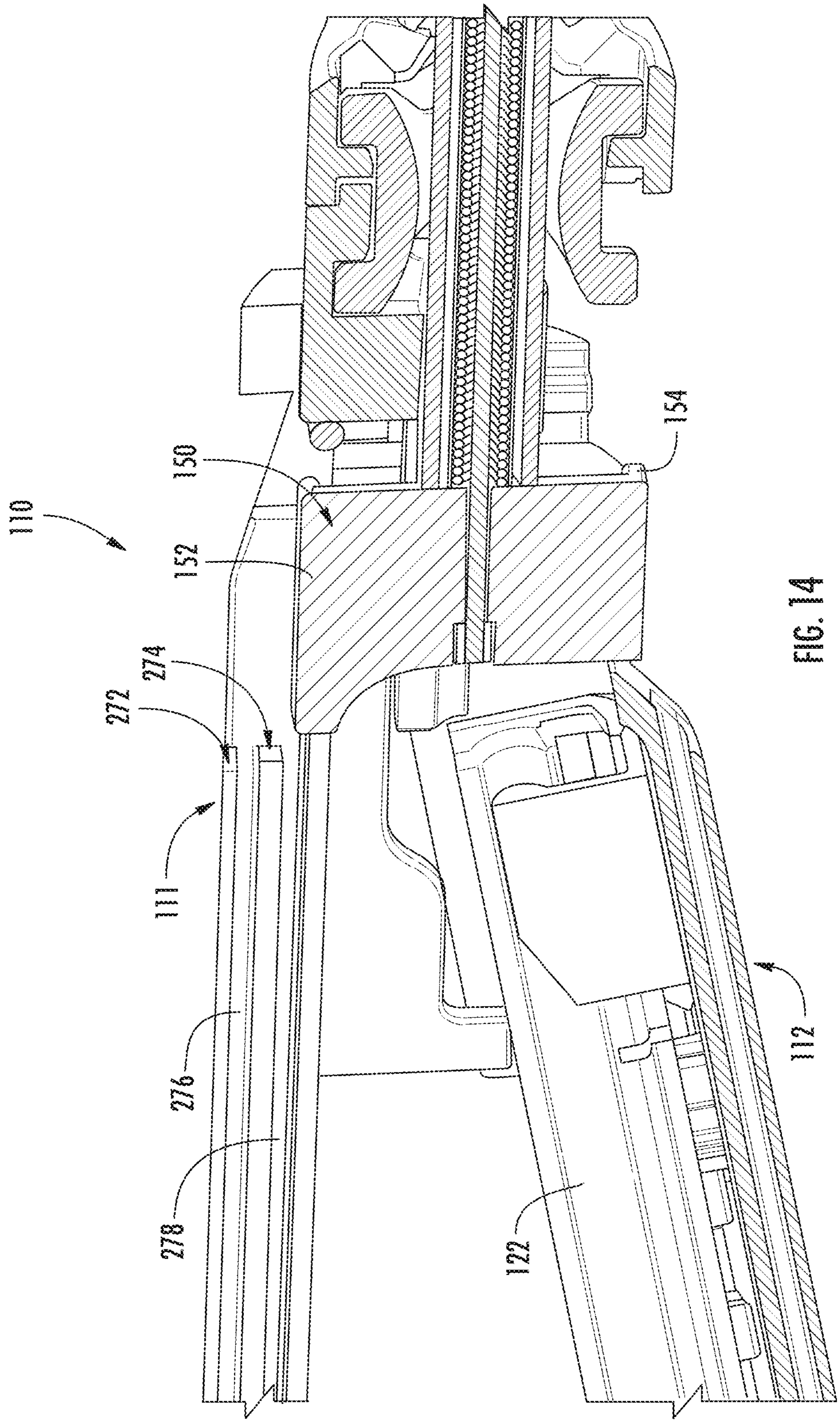
FIG. 14 is a partial cross-sectional view of a proximal portion of an end effector according to certain embodiments of the present disclosure.

Referring now to FIG. 14, another aspect of the invention comprises a system and method for setting multiple tissue gap distances for jaws 111, 112 in the closed position. In these embodiments, surgical instrument 100 may be used with suture cartridges 122 of differing sizes, e.g., taller or shorter staples. Alternatively, the surgeon may choose to set different tissue gap distances at selected portions of the surgical procedure (e.g., reduce the thickness of gap 206 during insertion/removal of the device and increase the thickness of gap 206 when clamping and/or stapling tissue).

Referring now to FIG. 14, another aspect of the invention comprises a system and method for setting multiple tissue gap distances for jaws 111, 112 in the closed position. In these embodiments, surgical instrument 100 may be used with suture cartridges 122 of differing sizes, e.g., taller or shorter staples. Drive member 150 and jaws 111, 112 cooperate with each other such that the upper surface of each of the staple cartridges remains at the same fixed distance from fixed jaw 111 regardless of the height of each of the staple cartridges. This allows the surgical instrument to have multiple settings for use with different staple cartridges, while still maintaining a fixed dimension between the jaws 111, 112 for clamping, stapling and/or sealing tissue. Alternatively, the surgeon may choose to set different tissue gap distances at selected portions of the surgical procedure (e.g., reduce the thickness of gap 206 during insertion/removal of the device and increase the thickness of gap 206 when clamping and/or stapling tissue).

In one embodiment, fixed jaw 111 comprises an inner surface 270 having first and second longitudinal projections 272, 274 extending substantially along the entire length of jaw 111. Projections 272, 274 define first and second longitudinal tracks or channels 276, 278 along inside surface 270 of jaw 111. Channels 276, 278 are preferably parallel and spaced from each other in a substantially perpendicular direction to the longitudinal axis of end effector 110. Channels 276, 278 are sized to receive upper shoe 152 of drive member 150 such that, when drive member 150 is translated distally, upper shoe 152 passes through one of the channels 276, 278. Lower shoe 154 of drive member 150 is preferably coupled to movable jaw 112. Alternatively, the first and second longitudinal channels may be formed in movable jaw 112 or staple cartridge 122 and sized to receive lower shoe 154 of drive member 150. In this embodiment, upper shoe 252 of drive member 150 may be coupled to fixed jaw 111. In both embodiments, drive member 150 may be aligned with one of the channels in movable jaw 112 to set the gap distance between jaws 111, 112.

Instrument 100 further includes an actuator or other suitable gearing mechanism (not shown) for moving drive member 150 upwards and downwards relative to jaw 111 such that upper shoe 152 is aligned with one of the channels 276, 278. The actuator may include a cable drive, rotatable drive member, push rod, wedge or other camming surface, screw rod, rack-pinion or other suitable mechanism for translating drive member 150 relative to channels 276, 278. The actuator and/or gearing mechanism may be coupled to drive member 150 and configured to translate drive member vertically upon distal or proximal movement of drive member 150. Alternatively, it may be coupled to a user interface on the proximal handle of instrument 100 or as part of a robotic control assembly and configured for direct user control of jaw settings. In one such embodiment, a rotatable gear mechanism (not shown) is configured to move jaw 111 up and down and to move a cam lock into position to lock the jaw 111 into a particular setting.

When drive member 150 is aligned with upper channel 276, the distance between lower surface 204 of jaw 111 and lower shoe 154 of drive member 150 is greater than the distance between these two components when drive member 150 is aligned with lower channel 278. This provides multiple settings or gap distances between jaws 111, 112. In one embodiment, these multiple settings may be used to load suture cartridges 122 having different heights. For example, a suture cartridge with relatively taller staples may be loaded into movable jaw 112 such that drive member 150 is automatically aligned with upper channel 276. In another example, a suture cartridge having shorter staples may be loaded into jaw 112 such that drive member 150 is aligned with lower channel 278. In this manner, the gap distance 206 between jaws 111, 112 can be substantially the same with suture cartridges having different heights (e.g., taller or shorter staples).

Of course, it will be recognized by those skilled in the art that the invention is not limited to two channels or tracks for drive member 150, and may include 3,4 or more channels depending on the number of differently-sized suture cartridges that are desired for use with the same surgical instrument. The invention may include a surgical instrument set (not shown) having a surgical instrument such as the one described herein and a plurality of different staple cartridges (only one type of staple cartridge 122 is shown in the figures). Each of the staple cartridges 122 are removably couplable to jaw 122 and may have different heights relative to the longitudinal axis of end effector 110. The end effector is configured such that the thickness of 206 gap between jaws 111, 112 will remain the same regardless of the height of the individual staple cartridge.

In an alternative embodiment, the multiple channel design may be used to change the tissue gap distance between jaws 111, 112 during a surgical operation. For example, drive member 150 may be aligned with upper channel 276 during insertion, removal and maneuvering of the instrument (to reduce the gap distance and the overall cross-sectional dimensions of end effector 110). Prior to or during actuation, drive member 150 may be translated downwards into alignment with lower channel 278 to increase the gap distance between jaws 11, 112 for clamping tissue.

In another embodiment, drive member 150 comprises a plurality of upper and/or lower shoes (not shown) that are situated parallel to each other, but offset in a direction substantially perpendicular to the longitudinal axis. In this embodiment, drive member 150 can be translated upwards or downwards such that one of the upper and/or lower shoes is aligned with one or more channels in jaws 111, 112. Similar to the above embodiments, drive member 150 may be translated with an actuator, gear drive, camming surface or other suitable mechanism to allow the drive member to be engaged at multiple settings, thereby defining multiple gap distances between jaws 111, 112. Alternatively, drive member 150 may have an upper or lower shoe that is movably coupled to the main body of drive member 150. In this configuration, the upper or lower shoe(s) may be translated vertically relative to body 151 and then fixed into a position that corresponds with one of the channels in end effector 110.

In yet another embodiment, staple cartridge 122 comprises a longitudinal channel (not shown) for receiving a portion of drive member 150, such as the upper or lower shoes, or another projection. In this embodiment, the vertical height of the channel in staple cartridge 122 will determine the gap distance between jaws 111, 112. Thus, staple cartridges 122 having different heights may be used with the same surgical instrument without changing the gap distance between jaws 111, 112. Alternatively, staple cartridges 122 with the same height may be designed with varying channel heights to vary the actual gap distance (depending on the desired clinical effect).

Figure 15:
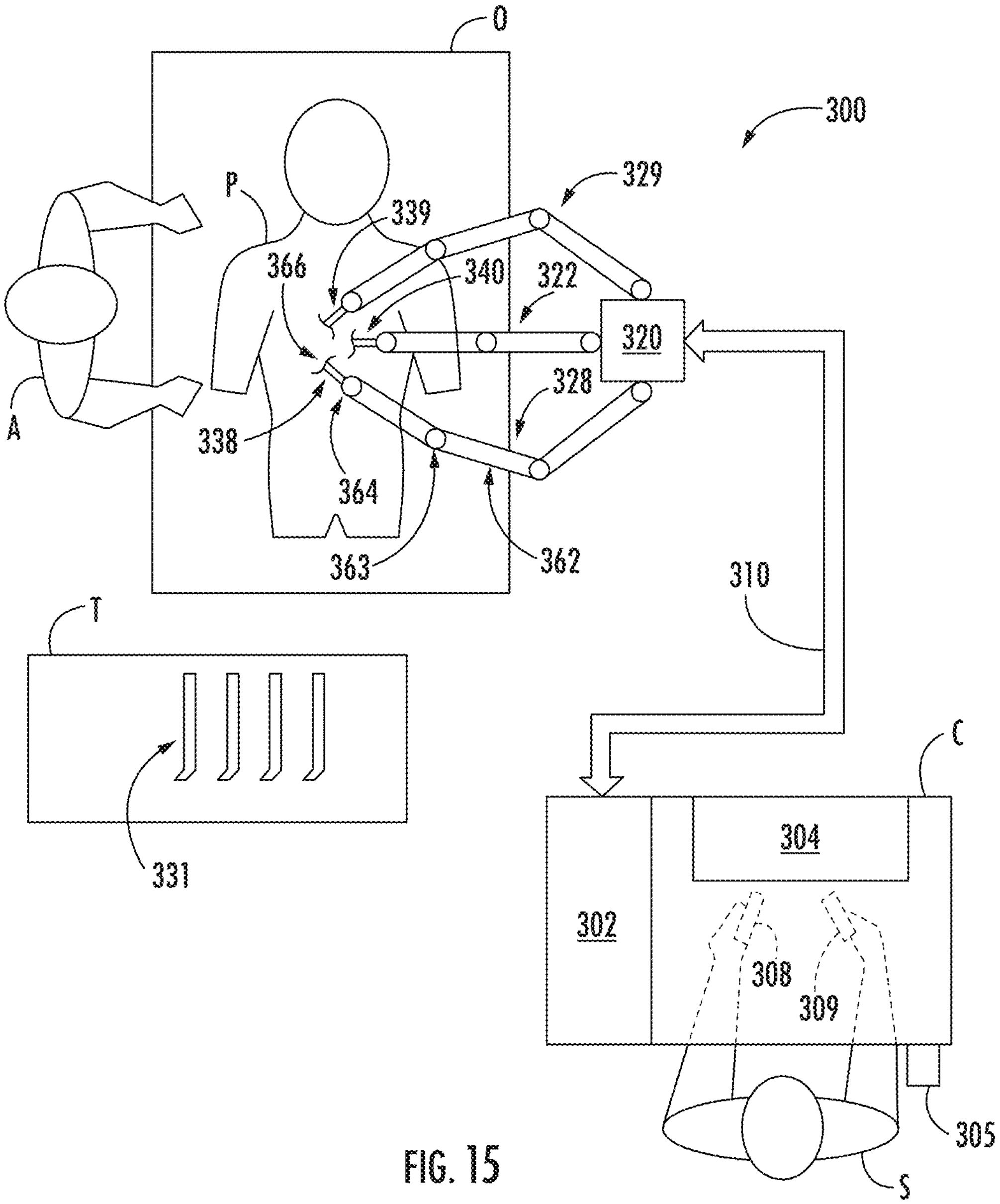
FIG. 15 illustrates a top view of an operating room employing a robotic surgical system utilizing aspects of the present invention.

FIG. 15 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One important function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware. For additional details on robotic surgical systems, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are hereby incorporated herein by reference in their entirety for all purposes.

Figure 16:
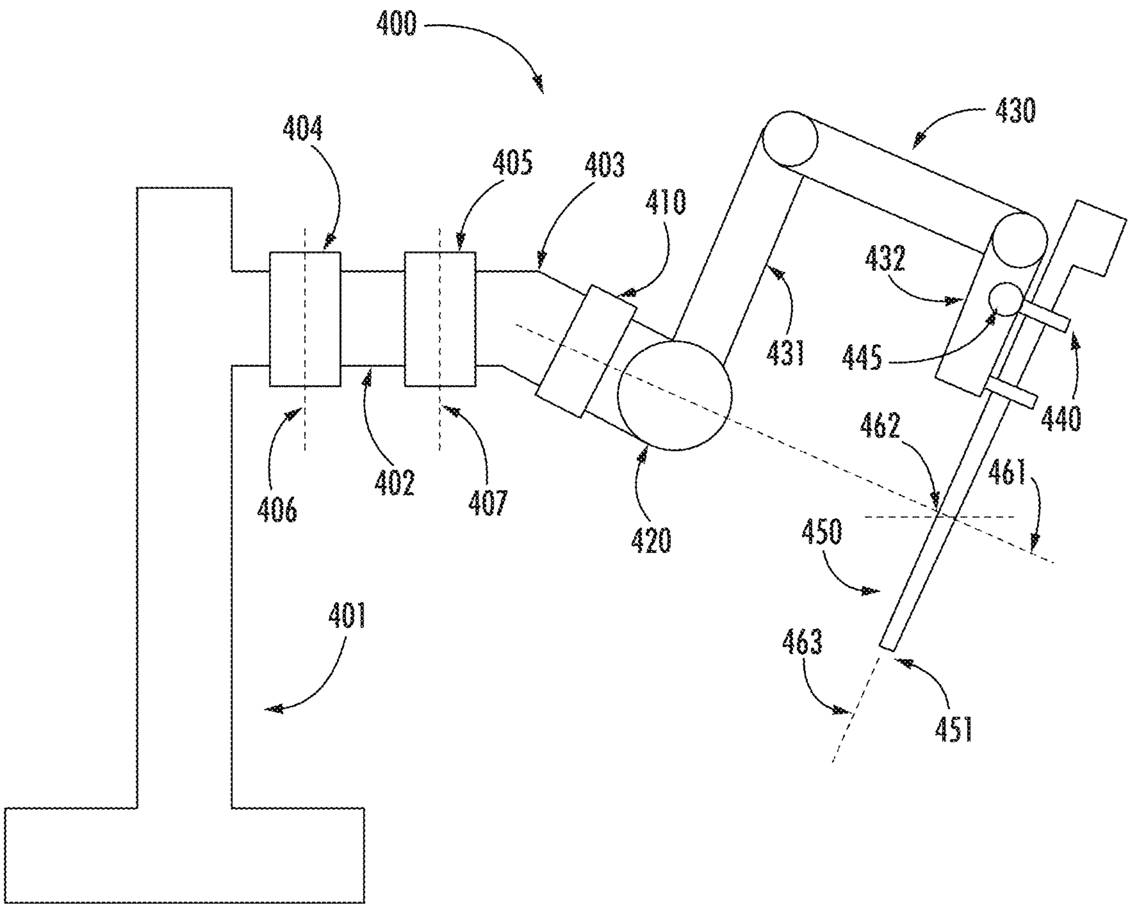
FIG. 16 illustrates a simplified side view of a robotic arm assembly that is usable with various aspects of the present invention.

FIG. 16 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403, which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407. Although only two links and two setup joints are shown in this example, more or less of each may be used as appropriate in this and other robotic arm assemblies in conjunction with the present invention. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator. A more complete description of illustrative robotic surgical systems for use with the present invention can be found in commonly-assigned U.S. Pat. Nos. 9,295,524, 9,339,344, 9,358,074, and 9,452,019, the complete disclosures of which are hereby incorporated by reference in their entirety for all purposes.

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A surgical instrument comprising:

a drive member having first and second projections; and an end effector comprising a first jaw and a second jaw, at least one of the first jaw and the second jaw being configured to move relative to the other of the first and second jaws to move the end effector from an open position to a closed position, wherein the first jaw defines first and second longitudinal slots each configured to accommodate the first projection of the drive member, wherein the first longitudinal slot is positioned a first distance relative to the second jaw and wherein the second longitudinal slot is positioned at a second distance relative to the second jaw, the first distance being different than the second distance, wherein the second jaw defines a third longitudinal slot configured to accommodate the second projection of the drive member;

wherein during a first operational mode, the first projection travels within the first longitudinal slot of the first jaw; and wherein during a second operational mode, the first projection travels within the second longitudinal slot of the first jaw.

2. The surgical instrument of claim 1, further comprising an actuator configured to switch between the first operational mode and the second operational mode.

3. The surgical instrument of claim 2, wherein the actuator comprises a camming surface configured to cooperate with the first projection of the drive member such that distal translation of the drive member moves the first projection from the first longitudinal slot to the second longitudinal slot.

4. The surgical instrument of claim 2, wherein the actuator comprises:

a cam mover plate having an opening defining an inclined camming surface; and an actuating mechanism coupled to the cam mover move plate and configured to move the first projection of the drive member between the first and second longitudinal slots.

5. The surgical instrument system of claim 2, wherein the jaws are in a first position when the first projection is translated through the first longitudinal slot and the jaws are in a second position when the first projection is translated through the second longitudinal slot.

6. The surgical instrument of claim 5, wherein the first and second jaws define a gap therebetween in the closed position, the gap extending substantially along a longitudinal axis of the end effector, and wherein the gap has a first thickness between the first and second jaws in the first position and the gap has a second thickness between the first and second jaws in the second position, the first thickness being greater than the second thickness.

7. The surgical instrument of claim 6, wherein the jaws are substantially parallel to each other in the first and second positions.

8. The surgical instrument of claim 6, further comprising a staple cartridge coupled to one of the first and second jaws and housing a plurality of staples.

9. The surgical instrument of claim 8, wherein the staple cartridge comprises a first staple cartridge removably couplable to the second jaw of the end effector, the instrument further comprising a second staple cartridge removably couplable to the second jaw of the end effector and comprising a plurality of staples, the first staple cartridge having a first height in a direction transverse to the longitudinal axis, the second staple cartridge having a second height in said direction, wherein the second height is less than the first height.

10. The surgical instrument of claim 9, wherein the first jaw has a lower surface and each of the staple cartridges has an upper surface, the first and second jaws defining a gap having a thickness between said upper and lower surfaces when one of the first and second staple cartridges is coupled to the second jaw and the jaws are in the closed position, wherein the end effector is configured such that the thickness of the gap is substantially equal when the first or the second staple cartridges are coupled to the second jaw.

11. The surgical instrument of claim 2, wherein the actuator comprises:

a cam pin extending from the first jaw; and a plate having a camming surface, wherein the plate is configured for translation in a longitudinal direction and the cam pin engages with the camming surface to cooperate with the first projection of the drive member such that distal translation of the drive member moves the first projection within the first longitudinal slot in the first operational mode and moves the first projection within the second longitudinal slot in the second operational mode.

12. The surgical instrument of claim 2, wherein the actuator further comprises a linkage coupling the first jaw with the drive member and comprising first and second coupling elements pivotable about a hinge to cooperate with the first projection of the drive member such that distal translation of the drive member moves the first projection within the first longitudinal slot in the first operational mode and moves the first projection within the second longitudinal slot in the second operational.

13. The surgical instrument of claim 2, wherein the actuator further comprises a rotatable drive member coupled to one of the first jaw or second jaw and configured such that rotation of the rotatable drive member moves the first projection of the first jaw between the first and second longitudinal slots.

14. A surgical instrument comprising:

a drive member having first and second projections; and an end effector comprising a first jaw and a second jaw, the end effector being configured to move between an open position and a closed position, wherein the first jaw defines first and second longitudinal slots each configured to accommodate the first projection of the drive member, wherein the second jaw defines a third longitudinal slot configured to accommodate the second projection of the drive member;

wherein during a first operational mode, the first projection travels within the first longitudinal slot of the first jaw;

wherein during a second operational mode, the first projection travels within the second longitudinal slot of the first jaw; and wherein the jaws are in a first position when the first projection is translated through the first longitudinal slot and the jaws are in a second position when the first projection is translated through the second longitudinal slot, and wherein the first and second jaws define a gap therebetween in the closed position, the gap extending substantially along a longitudinal axis of the end effector, and wherein the gap has a first thickness between the first and second jaws in the first position and the gap has a second thickness between the first and second jaws in the second position, the first thickness being greater than the second thickness.

15. The surgical instrument of claim 14, further comprising:

a first staple cartridge removably couplable to the second jaw of the end effector and comprising a first staple; and a second staple cartridge removably couplable to the second jaw of the end effector and comprising a second staple, the first staple cartridge having a first height in a direction transverse to the longitudinal axis, the second staple cartridge having a second height in said direction, wherein the second height is less than the first height.

16. The surgical instrument of claim 15, wherein the first jaw has a lower surface and each of the first and second staple cartridges has an upper surface, the first and second jaws defining a gap having a thickness between the upper surface of each of the first and second staple cartridges and the lower surface of the first jaw when one of the first and second staple cartridges is coupled to the second jaw and the jaws are in the closed position, wherein the end effector is configured such that the thickness of the gap is substantially equal when the first or the second staple cartridges are coupled to the second jaw.

17. A surgical instrument comprising:

a drive member having first and second projections; and an end effector comprising a first jaw and a second jaw, the end effector being configured to move between an open position and a closed position, wherein the first jaw defines first and second longitudinal slots each configured to accommodate the first projection of the drive member, wherein the second jaw defines a third longitudinal slot configured to accommodate the second projection of the drive member;

wherein during a first operational mode, the first projection travels within the first longitudinal slot of the first jaw;

wherein during a second operational mode, the first projection travels within the second longitudinal slot of the first jaw; and an actuator configured to switch between the first operational mode and the second operational mode, wherein the actuator comprises a camming surface configured to cooperate with the first projection of the drive member such that distal translation of the drive member moves the first projection from the first longitudinal slot to the second longitudinal slot.

18. The surgical instrument of claim 17, further comprising:

a first staple cartridge removably couplable to the second jaw of the end effector and comprising a first staple; and a second staple cartridge removably couplable to the second jaw of the end effector and comprising a second staple, the first staple cartridge having a first height in a direction transverse to a longitudinal axis of the end effector, the second staple cartridge having a second height in said direction, wherein the second height is less than the first height.

19. The surgical instrument of claim 18, wherein the first jaw has a lower surface and each of the first and second staple cartridges has an upper surface, the first and second jaws defining a gap having a thickness between the upper surface of each of the first and second staple cartridges and the lower surface of the first jaw when one of the first and second staple cartridges is coupled to the second jaw and the jaws are in the closed position, wherein the end effector is configured such that the thickness of the gap is substantially equal when the first or the second staple cartridges are coupled to the second jaw.

* * * * *